(12) United States Patent
Körner et al.

(10) Patent No.: US 11,231,269 B2
(45) Date of Patent: Jan. 25, 2022

(54) ARRANGEMENT AND METHOD FOR ROBUST SINGLE-SHOT INTERFEROMETRY

(71) Applicant: Universität Stuttgart, Stuttgart (DE)

(72) Inventors: Klaus Körner, Berlin (DE); Wolfgang Osten, Stuttgart (DE)

(73) Assignee: Universität Stuttgart, Stuttgart (DE)

( * ) Notice: Subject to any disclaimer, the term of this patent is extended or adjusted under 35 U.S.C. 154(b) by 171 days.

(21) Appl. No.: 16/468,037

(22) PCT Filed: Dec. 7, 2017

(86) PCT No.: PCT/EP2017/081832
§ 371 (c)(1),
(2) Date: Jan. 16, 2020

(87) PCT Pub. No.: WO2018/108697
PCT Pub. Date: Jun. 21, 2018

(65) Prior Publication Data
US 2020/0408505 A1    Dec. 31, 2020

(30) Foreign Application Priority Data

Dec. 13, 2016  (DE) ...................... 10 2016 014 802.0

(51) Int. Cl.
*G01B 9/02* (2006.01)
*A61B 5/00* (2006.01)
*G01B 9/04* (2006.01)

(52) U.S. Cl.
CPC .......... *G01B 9/0203* (2013.01); *A61B 5/0066* (2013.01); *G01B 9/02032* (2013.01);
(Continued)

(58) Field of Classification Search
CPC .............. G01B 9/0203; G01B 9/02049; G01B 9/02032; G01B 9/02091; G01B 2290/60;
(Continued)

(56) References Cited

U.S. PATENT DOCUMENTS 7,330,274 B2   2/2008  Hill
7,956,630 B1   6/2011  Chen
(Continued)

FOREIGN PATENT DOCUMENTS

DE   102010046907 A1   2/2012
DE   102010056122 B3   6/2012
(Continued)

OTHER PUBLICATIONS

Jun. 27, 2019—(WO) International Preliminary Report on Patentability—App PCT/EP2017/081832.
(Continued)

*Primary Examiner* — Jonathan M Hansen
(74) *Attorney, Agent, or Firm* — Banner & Witcoff, Ltd.

(57) ABSTRACT

The present invention relates to an arrangement and a method for single-shot interferometry which can be used for detecting distance, profile, shape, undulation, roughness or the optical path length in or on optically rough or smooth objects or else for optical coherence tomography (OCT). The arrangement comprises a light source, an interferometer, in which an end reflector is arranged in the reference beam path, and also a detector for detecting an interferogram. In the reference beam path of the interferometer, the end reflector can be embodied with three plane reflecting surfaces as a prism mirror or air mirror assembly in order to generate between reference and object beams a lateral shear of magnitude delta_q for obtaining a spatial interferogram. The embodiment of said assembly with regard to the angles and the arrangement of the reflecting surfaces makes possible a large aperture angle for a high numerical aperture. In the method, in the reference beam path it is possible to carry out a reduction of the aperture angle of the reference beam using beam-limiting means in order to achieve an optimum adaptation to the geometrically given aperture angle of the
(Continued)

Figure 1:
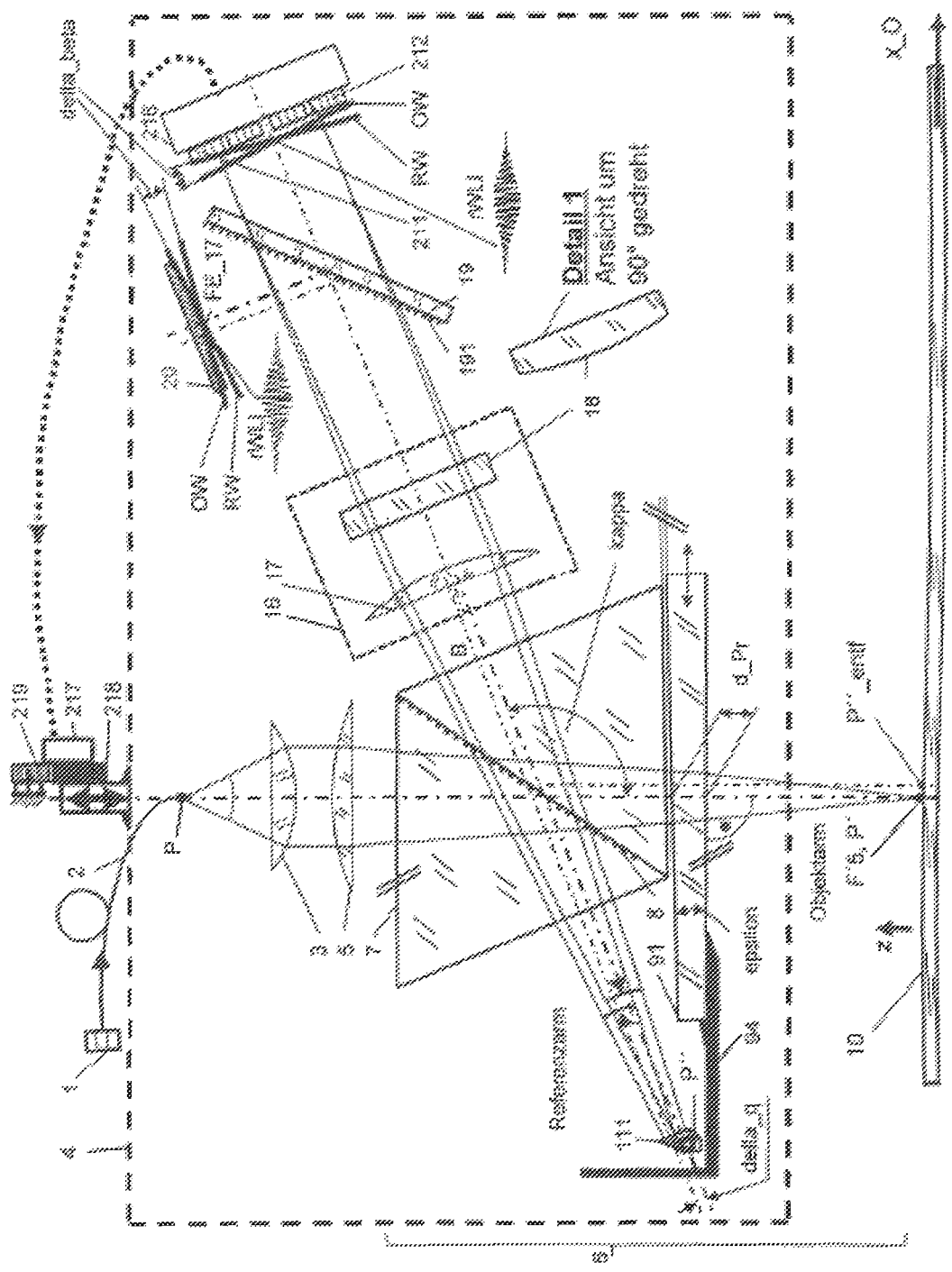

end reflector in the reference beam path, which is designed to be smaller than the aperture angle in the object beam path. The end reflector in the reference beam path can also be used as part of a second interferometer for high-resolution measurement of the displacement of the arrangement for single-shot interferometry, wherein said displacement serves for focusing. The end reflector is embodied as a triple reflection arrangement (e.g. a prism arrangement) having three reflecting surfaces. The triple reflection arrangement can have an M- or W-beam path, a non-intersecting zigzag beam path or an intersecting (zigzag) beam path.

21 Claims, 13 Drawing Sheets

(52) U.S. Cl.
CPC ..... *G01B 9/02049* (2013.01); *G01B 9/02091* (2013.01); *G01B 9/04* (2013.01); *G01B 2290/60* (2013.01)

(58) Field of Classification Search
CPC .... G01B 9/04; G01B 2290/15; G01B 9/0209; G02B 5/122; A61B 5/0066
See application file for complete search history.

(56) References Cited

U.S. PATENT DOCUMENTS

| | | |
|---|---|---|
| 2003/0048456 A1 | 3/2003 | Hill |
| 2011/0235056 A1 | 9/2011 | Matsudo et al. |
| 2012/0307258 A1 | 12/2012 | Koerner et al. |
| 2015/0077760 A1 | 3/2015 | Koerner et al. |
| 2016/0320598 A1* | 11/2016 | Dubois ................ G02B 21/33 |

FOREIGN PATENT DOCUMENTS

| | | |
|---|---|---|
| EP | 2526373 B1 | 12/2013 |
| EP | 2843360 A1 | 3/2015 |

OTHER PUBLICATIONS

Feb. 9, 2018—(PCT) International Search Report and Written Opinion—App PCT/EP2017/081832.

* cited by examiner

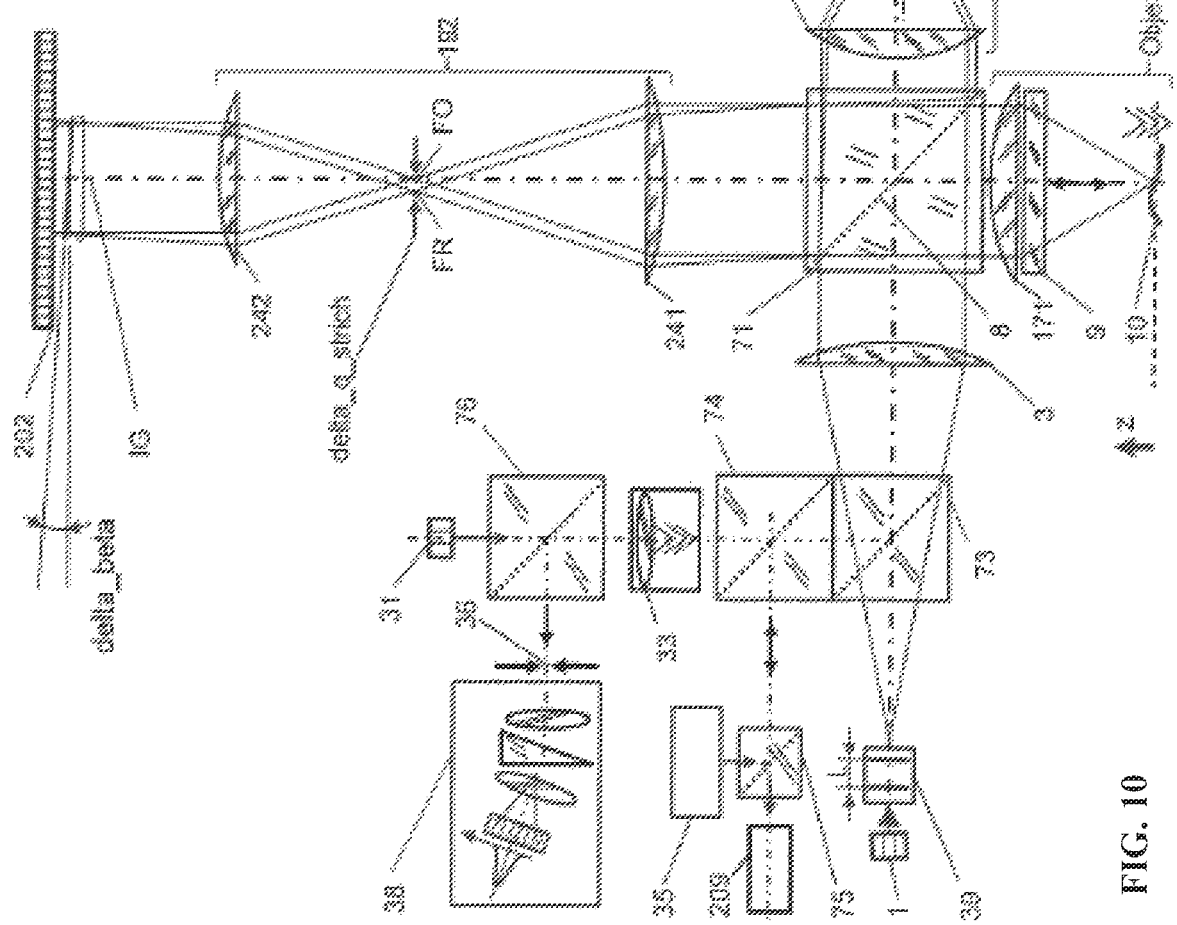
FIG. 10
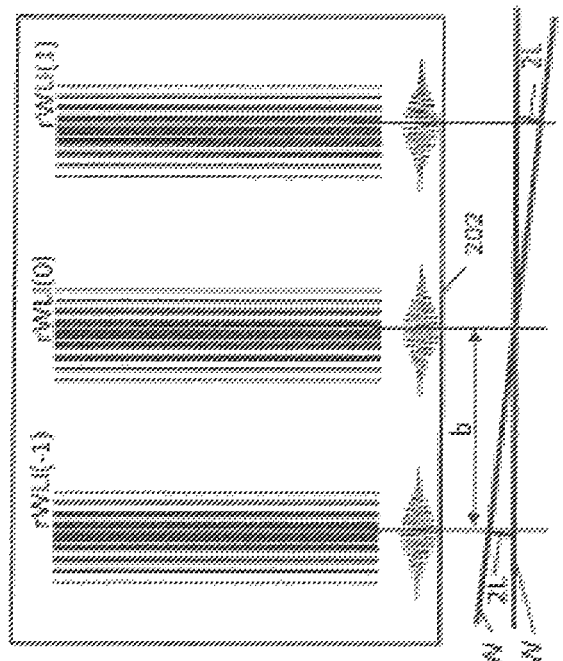
FIG. 11
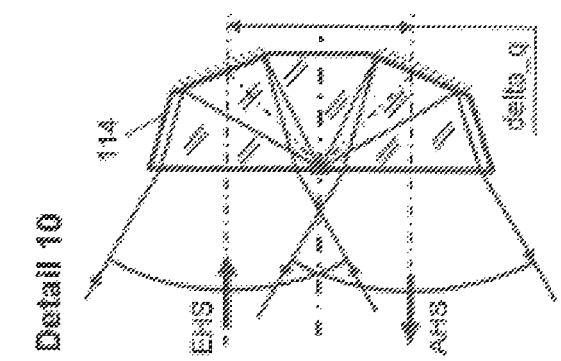
Detail 10

ARRANGEMENT AND METHOD FOR ROBUST SINGLE-SHOT INTERFEROMETRY

The present application is a U.S. National Phase of International Application No. PCT/EP2017/081832, filed on Dec. 7, 2017, designating the United States of America, and claims priority to German Patent Application No. 10 2016 014 802.0, filed Dec. 13, 2016. This application claims priority to and the benefit of the above-identified applications, each of which is fully incorporated by reference herein.

The present invention relates to an arrangement and a method for single-shot interferometry for detecting distance, profile, shape, waviness, roughness or optical path length in or on optically rough or smooth objects and/or for optical coherence tomography (OCT).

An arrangement and a method for single-shot interferometry are known e.g. from the patent specification EP 2 843 360 A1. In the case of the interferometric approaches described in EP 2 843 360 A1, there occurs a wavefront inversion that places particularly high demands on the upstream beam-shaping optical system for low-error measurement on the basis of mutually inclined interfering wavefronts or wavefronts with curvature and lateral shear. These requirements exist in particular with regard to low wavefront aberrations. Further interferometric approaches are e.g. known from the patent specifications EP 2 526 373 B1 and DE 10 2010 056 122 B3. These approaches are based on end reflector arrangements in the reference beam path of an interferometer with three plane mirrors and with a crossed beam path. In the patent specifications EP 2 526 373 B1 and DE 10 2010 056 122 B3, however, there is no indication as to how a large aperture angle for a comparatively high numerical aperture N.A. is to be achieved, for example for a numerical aperture N.A.=0.4. However, a numerical aperture N.A. in this size range is indispensable for ensuring a high lateral resolution in the range of one micrometer and also slightly below for visible light.

It is an object of the invention to provide improved arrangements and methods for the commercial use of single-shot interferometry with a spatial interferogram, in particular on the basis of mechanically robust optical interferometer components.

In particular, the invention is based on the object to significantly increase the numerical aperture of an interferometric measuring arrangement, in particular for single-shot interferometry with a spatial interferogram in comparison to the prior art, wherein the robustness of the arrangement is ensured. This is to be made possible with end reflector assemblies in a two-beam interferometer, which can be manufactured both classically optically by polishing techniques and with printing techniques or, in the case of air-mirror assemblies, by metallic components and by means single-point diamond machining.

Therefore, it is another object to provide optical assemblies that are technically easy to manufacture, that are robust enough for use in a manufacturing environment and/or that can also be used for inline measurement in a mechanical production line. Furthermore, the object of measuring a displacement in the z-direction of the single-shot interferometer is to be solved.

This/These object(s) is/are achieved by an arrangement for robust two-beam interferometry according to claim 1 or 6 and by a method for robust two-beam interferometry according to claim 18 or 22. Preferred embodiments are subject of the dependent claims.

In particular, an arrangement and a method for single-shot interferometry are proposed, which are suitable for detecting distance, profile, shape, waviness, roughness or the optical path length in or on optically rough or smooth objects and/or can also be used for optical coherence tomography (OCT). The arrangement comprises a light source, an interferometer, in which an end reflector is arranged in the reference beam path, and a detector for detecting an interferogram. In the reference beam path of the interferometer, the end reflector can be formed with three plane reflecting surfaces as a prism mirror or as an air mirror assembly in order to generate a lateral shear of the amount delta_q between reference and object beams for obtaining a spatial interferogram. The formation of this assembly with respect to the angles and the arrangement of the reflecting surfaces allows a large aperture angle for a high numerical aperture. In the method, a reduction of the aperture angle of the reference beam can be performed in the reference beam path with beam-limiting means in order to achieve an optimal adaptation to the geometrically given aperture angle of the end reflector in the reference beam path, which is smaller than the aperture angle in the object beam path. The end reflector in the reference beam path can also be used as part of a second interferometer for high-resolution measurement of the displacement of the arrangement for single-shot interferometry, this displacement serving for focusing.

The end reflector is formed as a triple reflection arrangement (e.g. a prism arrangement) having three reflecting surfaces. The triple reflection arrangement can have an M or W beam path, a non-crossing zigzag beam path or a crossing (zigzag) beam path.

In particular, according to a first embodiment, an arrangement for robust two-beam interferometry is provided, e.g. an arrangement for detecting distance, depth, profile, shape, waviness and/or roughness or the optical path length in or on rough or optically smooth technical or biological objects, also in layer form, and/or for optical coherence tomography (OCT).

The arrangement comprises the following:

a source of short-coherent electromagnetic radiation for illuminating the object, an interferometer, in particular also in the form of an interference microscope, with an object beam path and with at least one reference beam path and a measurement plane in the object beam path, in which the surface or volume elements of the object to be optically measured are at least approximately located; as well as at least one rasterized detector for detecting electromagnetic radiation in the form of at least one spatial interferogram, wherein:

at least one end reflector is arranged in the reference beam path of the interferometer as a reference reflector, wherein the end reflector is formed as a triple reflection arrangement with three reflecting surfaces.

The three reflecting surfaces are each at least approximately perpendicular to a common reference plane BE. The three track lines of the planes, which are represented by the three reflecting surfaces, form a triangle ABC with an obtuse angle in the reference plane BE, so that in this interferometer a lateral shear of the amount delta_q exists between reference and object beams. The first reflecting surface lies on a straight line on which the points C and B lie, the second reflecting surface lies on an (extended) straight line on which the points A and C lie, and the third reflecting surface lies on an (extended) straight line on which the points A and B lie. The three reflecting surfaces may be plane surfaces, e.g. be plane-mirror surfaces.

Furthermore, the following features are observed:

The beam path of the triple reflection arrangement is crossed.

The second reflecting surface, lying on an extended straight line m including points A and C, is used as the second (in the reflection order) of the three reflecting surfaces for reflection of a focused beam FB.

The first reflecting surface including points C and B and the second reflecting surface are disposed at an acute angle relative to each other. For example, the reflecting surface including points C and B may abut the second reflecting surface at an acute angle. Thus, the angle ACB is an obtuse angle.

The first (plane) reflecting surface including points C and B is used as the first or third (in the reflection order) of the three plane reflecting surfaces for reflecting the beam FB.

Further, there is a normal N_m from the point B to the second reflecting surface through which the straight line m passes.

The first reflecting surface including points C and B and the third reflecting surface including points A and D form an obtuse angle CBD. Thus, the angle ABC is an acute angle.

For the triple reflection arrangement with the crossed beam path, there is an angle gamma between marginal ray RAS of the incoming or outgoing beam and the second reflecting surface, and for the magnitude of the angle gamma it holds that <12° (degrees).

Furthermore, for the magnitude of the angle gamma is preferably <5° (degrees). Furthermore, the angle gamma is preferably at least approximately 0° (degree). The latter results in a comparatively large aperture angle of the focused beam, which can still pass through the triple reflection arrangement.

Furthermore, the beam focus BF can preferably lie at least approximately on the normal N_m and at least approximately in the vicinity of the second reflecting surface.

Furthermore, the triple reflection arrangement can be formed as an air mirror group or as a prism mirror group.

For the prism, a glass material can be used, which can preferably be of higher refractive index, in order to be able to process the highest possible aperture angle for the focused beam in the prism mirror group. For example, the refractive index of the glass material may be about 1.85. This is of particular interest for use in a Mirau interferometer with a 0.55 numerical aperture. The prism mirror group may be formed as a mini or micro prism, i.e. as a refractive component with three reflections. Such a mini or micro prism is comparatively easy to manufacture and represents a monolith.

As a rule, the air mirror group cannot be manufactured as a monolith, but as an assembled assembly. Such an assembled assembly builds—with the same parameters— usually larger than a monolithic mini or micro prism or larger than a refractive component.

The reflecting surface used by the focused beam FB on an extended straight line k including points A and B (third reflecting surface) is preferably more than three times as long as the second reflecting surface on an extended straight line m including points A and C.

Furthermore, the triple reflection arrangement is preferably formed with a signed angle tau smaller than −1°, i.e. −2° to −20°. The angle tau is the angle between the input main ray in the end reflector or in the triple reflection arrangement and the second reflecting surface.

A further embodiment relates to an arrangement for robust two-beam interferometry for detecting distance, depth, profile, shape, waviness and/or roughness or the optical path length in or on technical or biological objects, also in layer form, and/or for optical coherence tomography (OCT). The arrangement comprises the following:

a source of short-coherent electromagnetic radiation for illuminating the object, an interferometer, in particular also in the form of an interference microscope, with an object beam path (O), at least one reference beam path (R) and a measurement plane in the object beam path, in which the surface or volume elements of the object to be optically measured are at least approximately located; as well as at least one rasterized detector for detecting electromagnetic radiation in the form of at least one spatial interferogram, wherein:

at least one end reflector is arranged in the reference beam path (R) of the interferometer as a reference reflector, wherein the end reflector is formed as a triple reflection arrangement with three reflecting surfaces, and the three reflecting surfaces are each at least approximately perpendicular to a common reference plane BE, and the three track lines of the planes, which are represented by the three reflecting surfaces (which may be plane mirror surfaces), form a triangle ABC with an obtuse angle in the reference plane BE. Here, the first reflecting surface lies on an (extended) straight line on which the points C and B lie, the second reflecting surface lies on an (extended) straight line m on which the points A and C lie, and the third reflecting surface lies on an (extended) straight line k, on which the points A and B lie.

The characteristic features for the largest possible aperture angle alpha of a focused beam for all triple reflection arrangements with plane mirror surfaces are mentioned below:

The triple reflection arrangement is formed as a prism mirror group.

The triple reflection arrangement is formed either with a W beam path or with a crossed beam path.

The reflecting surface lying on an extended straight line m including points A and C (the second reflecting surface) is used as the second of the three reflecting surfaces (in the order of reflections) for reflecting a focused beam FB.

The first reflecting surface and the second reflecting surface are arranged at an acute angle relative to each other. For example, the first reflecting surface including points C and B may abut the second reflecting surface at an acute angle. Thus, the angle ACB is an obtuse angle.

The reflecting surface including points C and B (the first reflecting surface) is used as the first or the third (in the order of reflections) of the three reflecting surfaces for reflection.

There is a normal N_m from point B, perpendicular to the second reflecting surface, through which the straight line m passes.

The first reflecting surface including points C and B and the third reflecting surface on an extended straight line k, which includes points A and B, form an obtuse angle. Thus, the angle ABC is an acute angle.

Furthermore, the beam focus BF is preferably at least approximately on the normal N_m and at least approximately in the vicinity of the second reflecting surface.

Furthermore, the light source is preferably formed as a frequency comb laser with a micro-cavity.

Furthermore, there is preferably at least one depth measuring system in the object measuring field for detecting the measuring object in a predetermined (for example coarser) scale, wherein the depth measuring system is arranged with its beam path at least approximately coaxial with the interferometric beam path. The depth measuring system is preferably formed to be chromatic-confocal.

Furthermore, the interferometer in the reference arm can be assigned an attenuation filter with a maximum of the transmission in the center of the attenuation filter for reducing the aperture angle of the reference beam.

The attenuation filter in the reference arm is used to reduce the diameter of the reference beam or the aperture angle of the reference beam such that the numerical aperture predetermined by its geometry and possibly the refractive index in case of a prism design of the triple reflection assembly is not exceeded. Preferably, the numerical aperture in the reference arm of the interferometer can be reduced to half. However, this does not lead to a disadvantage in an interferometer arrangement with a comparatively high numerical aperture in the object arm, since the spatial interferogram occurs approximately in the middle of the mutually inclined wavefronts due to the small wave-optical depth of field and the reconciliation of the optical path lengths. Because of the preferably short-coherent light source, the significant modulations occurring in the spatial interferogram are less than 20.

The tilting of the two interfering wavefronts is preferably made so great by the size of the lateral shear delta_q that the extent of the spatial interferogram is preferably less than one third of the lateral extent of the object wavefront.

Furthermore, the attenuation filter is preferably formed with a radially symmetric Gaussian characteristic. This is advantageous for the formation of wavefronts.

Furthermore, the attenuation filter is preferably formed with a one-dimensional characteristic.

On the reflecting surface of a triple reflection assembly or arrangement, which includes points B and D, there is preferably a grazing incidence at least for the marginal ray of a beam with an incidence angle of greater than 75° (degrees). Thus, for the reference beam, a comparatively large aperture angle, for example of 17.5° (degrees) and thus a comparatively large numerical aperture N.A. of 0.3 can be achieved in case of an air arrangement.

Furthermore, the interferometer, the detector and optionally other optical elements can be arranged within a sensor head. The sensor head is preferably associated with a highly dynamic actuating system with an assigned high-resolution depth measuring system, wherein the actuating system always keeps the sensor head at each cooperative measurement point in the wave-optical depth of field in real time. The actuating system is preferably a piezo actuator system, which preferably receives the control signal from the WLI signal (WLI: white light interferogram). Preferably, however, use is also made of the depth measurement signal of a preferably chromatic-confocal sensor operating in a predetermined (for example, coarser) depth-measuring scale, which is arranged coaxially to the measurement beam path. The separation of the signals is done by color separators.

Furthermore, the angle kappa in a Michelson interferometer is preferably between 96° (degrees) and 140° (degrees). The angle exists between the optical axis of the object beam path in the interferometer and the optical axis of the beam path at the output of the interferometer. An interferometer configuration deviating from 90° (degrees) creates more space at the output of the interferometer.

Further, preferably, for adjustment, a laterally slidable (e.g., slender) glass wedge having a center thickness d_Pr is disposed in the object arm and on the optical axis of the microscope objective of a two-beam interferometer, with which the glass path length of the reference arm of the two-beam interferometer is compensated to zero. The maximum thickness d_Pr of the glass wedge may be in the range of 1 mm to 2 mm. With a stable structure of the interferometer, this adjustment must be done only once.

Preferably—if the three-reflecting-surfaces prism is arranged in the reference arm—this center thickness d_Pr of the slidable glass wedge at least approximately corresponds to the glass path length of the three-reflecting-surfaces prism. By adjustment with the aid of the glass wedge, the optical path difference (OPD) of the reference arm and of the object arm can be minimized, e.g. be reduced to less than 2 µm. Thus, there is a very well adjusted, balanced interferometer with respect to the optical path difference, which can deliver a symmetrical spatial white light interferogram (rWLI) at least on axially perpendicular mirror surfaces.

According to a further aspect of the invention, a method for robust two-beam interferometry for detecting distance, depth, profile, shape, waviness and/or roughness or the optical path length in or on technical or biological objects, also in layer form, or also for optical coherence tomography (OCT) is proposed.

The method comprises providing an arrangement for robust two-beam interferometry (e.g., one of the arrangements previously described), the arrangement comprising the following:

a source of short-coherent electromagnetic radiation for illuminating the object, a (white light) interferometer, in particular also in the form of an interference microscope, with an object beam path, at least one reference beam path, in which at least one end reflector is arranged, and a measurement plane in the object beam path, in which the surface or volume elements of the object to be optically measured are at least approximately located, as well as at least one rasterized detector for detecting electromagnetic radiation in the form of at least one spatial interferogram, wherein:

in the reference beam path of the interferometer, at least one end reflector having three reflecting surfaces is arranged as a reference reflector, wherein the end reflector has three reflecting surfaces, which are each at least approximately perpendicular to a common reference plane. The end reflector may be formed as one of the above-described triple reflection arrangements.

Furthermore, in the reference beam path, a reduction of the aperture angle of the reference beam is performed with beam-limiting means. The reduction of the aperture angle of the reference beam is preferably achieved by a beam attenuation with a radially symmetric filter or a one-dimensional filter.

This is advantageous because in this interferometer, a reference end reflector can be used, which can process a significantly lower numerical aperture than is given in the object beam path. The high numerical aperture in the object beam path is needed for the interferometric measuring arrangement only for the object beam to form a fine diffraction-limited scanning spot on the object. This is of utmost importance for precision-machined surfaces that are not mirrors in engineering.

The reduction of the aperture angle of the reference beam with beam-limiting means is preferably carried out at least approximately in the Fourier plane of an objective in the reference beam path of a Linnik interferometer. Thus, the shadowing of the beams is minimized, since in the Fourier plane beams having a lateral shear in the object space overlap.

In order to form the balance signal or control signal for the focus control of the (white light) interferometer, the amounts I_left and I_right of the intensities of adjacent photoelements of a photodiode detector or pixels of a rasterized detector, which are located to the left from the spatial white light interferogram and to the right from a reference point RP, can be determined and summed up by an electronic arithmetic unit. The reference point RP is usually on the optical axis. The sum S_left of the amounts I_left and the sum S_right of the amounts I_right are subtracted from one another, and from this the signed control signal (balance signal) is derived. Preferably, it is set to zero. The electronic arithmetic unit can be formed as a digital signal processor.

The interferometer, the detector and optionally further optical elements can be arranged within a sensor head. The sensor head is preferably associated with electromechanical high-dynamic means for depth tracking of the sensor head, which always keep the sensor head at each cooperative measurement point in the wave-optical depth of field in measurement real time. The measurement result is always formed from the signed addition of the depth measurement value of the tracking depth measurement system and the depth measurement value z_rWLI. The depth measurement value z_rWLI is determined by a spatial white light interferogram or from the spatial white light interferogram signal or rWLI signal.

Another method for robust two-beam interferometry for detecting distance, depth, profile, shape, waviness and/or roughness or the optical path length in or on technical or biological objects, also in layer form, or also for optical coherence tomography (OCT) with formation of a white light spatial interferogram comprises:

providing an arrangement for robust two-beam interferometry (for example, one of the arrangements described above), the arrangement comprising the following:

a source of short-coherent electromagnetic radiation for illuminating the object, a first interferometer, in particular also in the form of an interference microscope, with an object beam path, at least one reference beam path and a measurement plane in the object beam path, in which the object is located, as well as at least one rasterized detector for detecting electromagnetic radiation in the form of at least one spatial interferogram, wherein:

in the reference beam path of the interferometer, at least one end reflector having three reflecting surfaces is arranged as a reference reflector and the three reflecting surfaces are each at least approximately perpendicular to a common reference plane. The end reflector may be formed as one of the above-described triple reflection arrangements.

Furthermore, a second optical scanning of the end reflector with the three reflecting surfaces is performed by a second separate interferometer with a laser light source in order to be able to measure a displacement in the z direction of the first interferometer belonging to the end reflector. The interferometer is rigidly connected to the end reflector and is operated as a single-shot interferometer. The single-shot interferometer with the source of short-coherent electromagnetic radiation is preferably designed as a Mirau interferometer. In the reference arm of the second separate interferometer, a triple reflector in the form of a room corner is preferably arranged. The reference arm of the second separate interferometer is preferably formed with a beam splitter, which in the first interferometer is used only as a coupling and decoupling beam splitter. The interfering beams of the second interferometer leave the beam splitter again on its input side. With this approach, the displacement z_1 of the first interferometer—as a compact arrangement—can be measured in the z-direction. Thus, from the value z_WLI, which is determined by the first interferometer, and the z_1 value, a position for an object point with respect to a component of the second separate interferometer can be calculated, for example with respect to a beam splitter of the second separate interferometer arranged in the optical system, which is used as a coupling and decoupling beam splitter in the first interferometer. The z_1 value results from the change in the optical path difference in the second interferometer, which is measured in a time-resolved manner and can be converted into a path signal in a manner known to the person skilled in the art. When the measuring process with the first interferometer is started, the z_1 value can be set to zero. Subsequently, the change in the optical path difference is determined continuously. When the measuring process with the first interferometer is started, however, any position value in millimeters can also be assigned to the z_1 value. Another possibility is to assign a white light source to the second interferometer and to generate a reference signal from the white light interferogram at the optical path difference zero.

Further Features and/or Advantages of the Invention

Preferably, further single-shot measurement points are used, preferably according to the chromatic-confocal approach, to keep the interferometric measurement point or the interferometric measurement points in a comparatively small measurement range for the measuring distance by a fast control system, since this measuring distance only has a few microns of depth range at a higher numerical aperture.

Preferably, an entire field of single-shot measurement points in line or matrix arrangement, preferably according to the chromatic-confocal approach, can be scanned with chromatic confocal sensors in addition. In this case, the depth resolution of a chromatic-confocal sensor is preferably better than one fifth of the wave-optical depth of field, and the measurement range is preferably at least five times the wave-optical depth of field of the beam path in the object arm of the interferometer.

The arrangement features of the single-shot measurement points in a matrix arrangement, preferably according to the chromatic-confocal approach, are preferably based on features of the patent DE 10 2006 007172 B4.

Preferably, the depth resolution of a chromatic-confocal sensor is better than one tenth of the wave-optical depth of field, and the measurement range is at least 100 times the wavelength of the wave-optical depth of field.

A line-like single-shot measurement is performed with the proposed arrangements with appropriate design of the sensor with cylinder optics preferably with a line-like light source and cylinder optics and a fast area camera.

A chromatic confocal sensor is preferably arranged coaxially to the interferometric sensor beam path in the object space.

A chromatic-confocal sensor is preferably arranged as a flow sensor in the interferometric sensor beam path in the object space. In this way, the control system on a three-coordinate measuring machine obtains in advance information about the measuring distances to be expected for the upcoming measurement run over the measurement object, and the interferometric sensor head is always adjusted accordingly in time, i.e. in process real time.

Furthermore, a line or matrix of chromatic-confocal point sensors, which operate on a coarser scale compared to interferometric measurement, is preferably arranged. The information thus obtained is used among others for the distance control in process real time and the "exploration" of the measurement environment in process real time.

In addition, a CMOS area camera for observing the measurement field is preferably used.

As already described in EP 2 626 373 B1, this approach can be operated with a frequency comb laser with a miniaturized resonator cavity. This has the advantage that also an unbalanced interferometer—with regard to the optical path length—can be used, since the required compensation of the optical path length—in simplified terms—is placed into the frequency comb laser.

Figure 2:
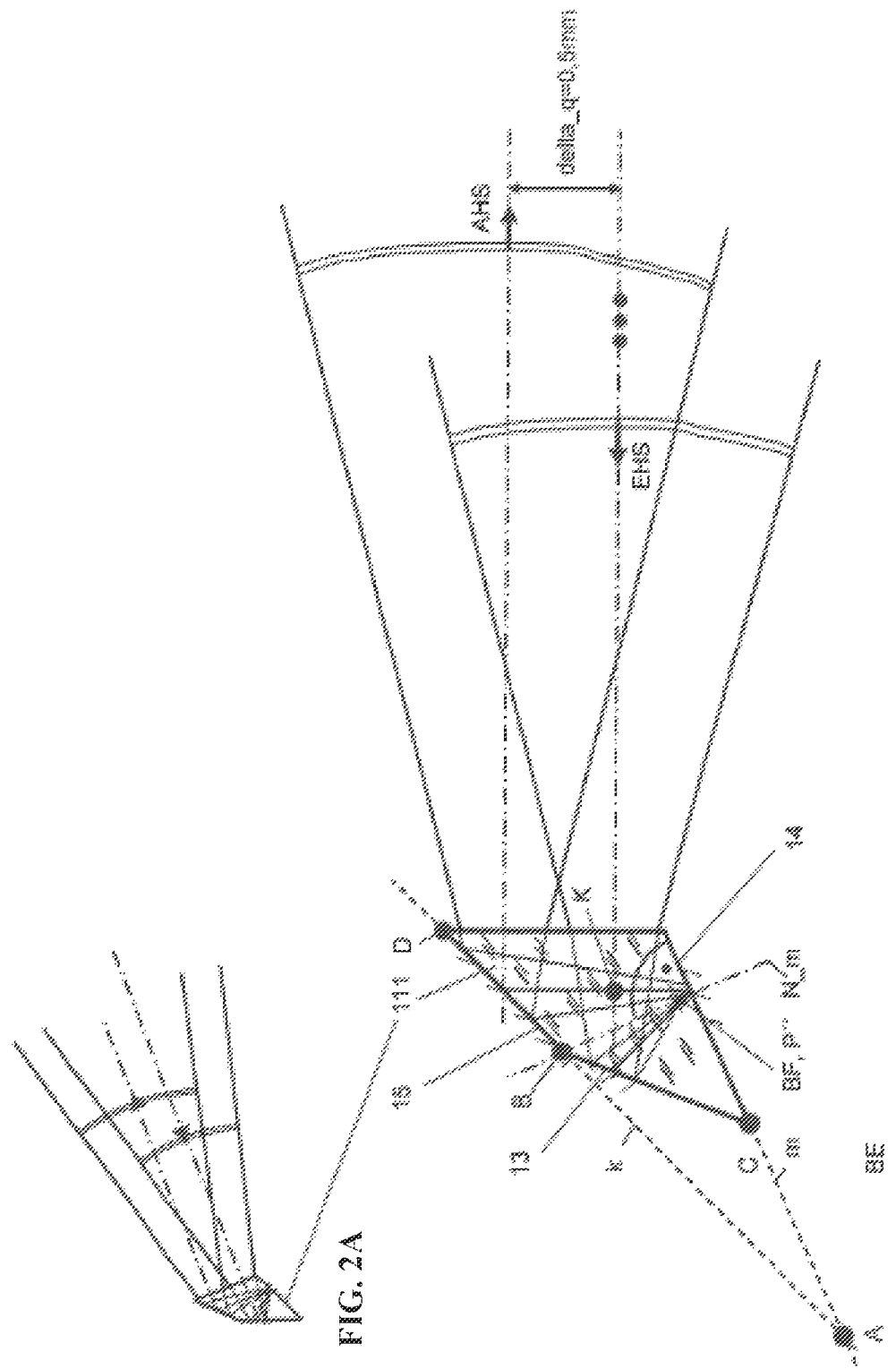
Figure 3:
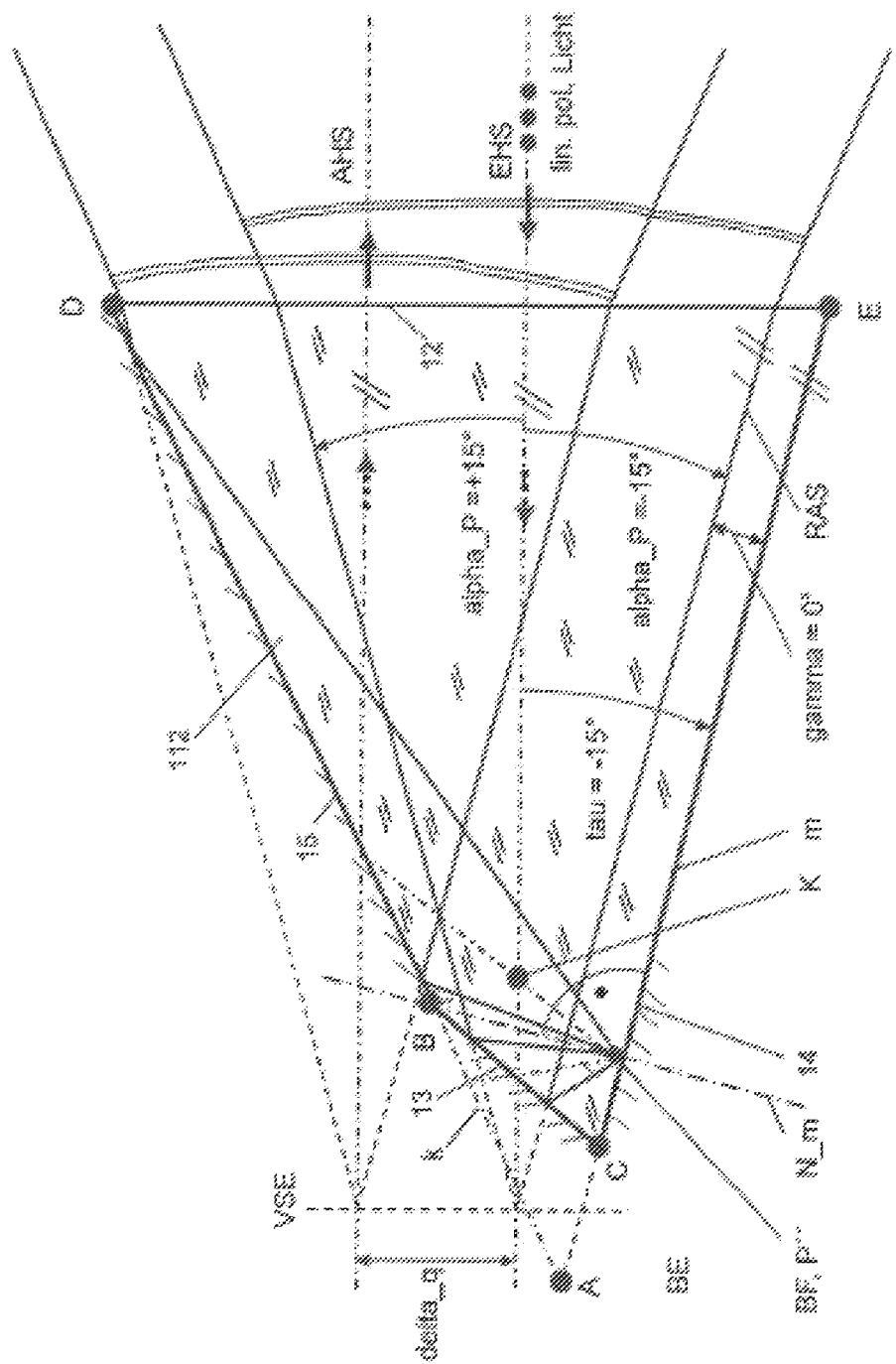
Figure 4:
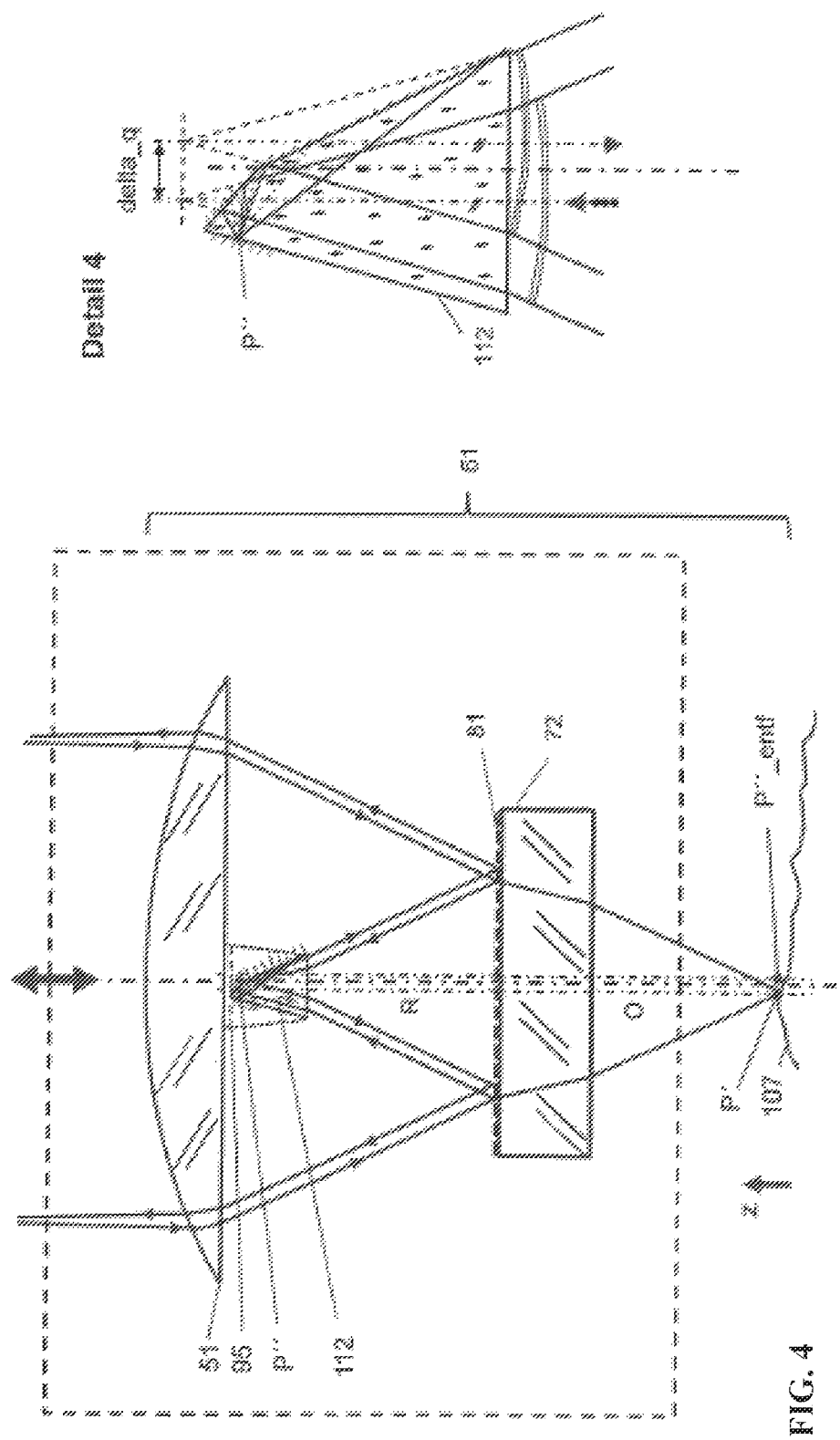
Figure 5:
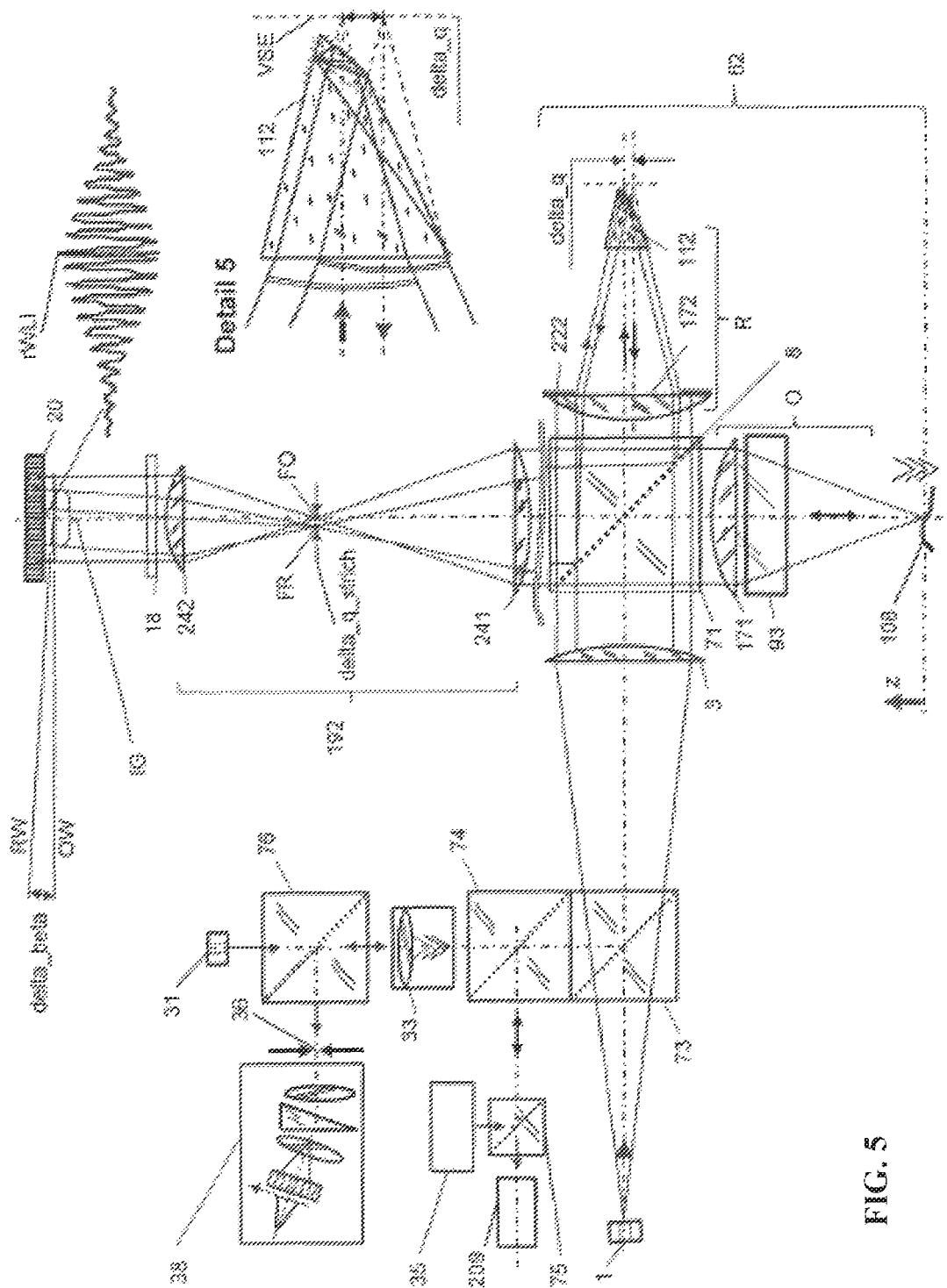
Figure 6:
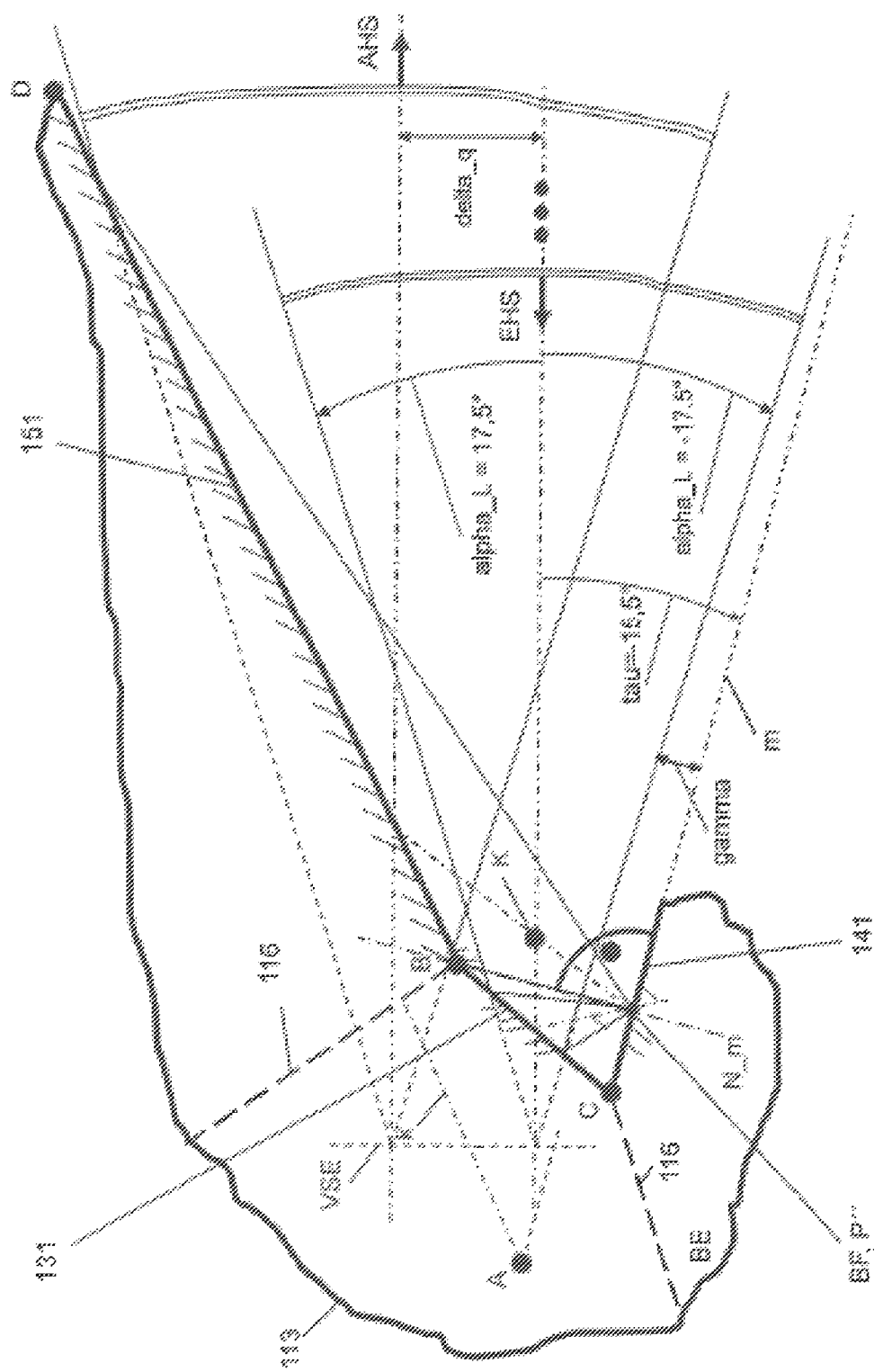
Figure 7:
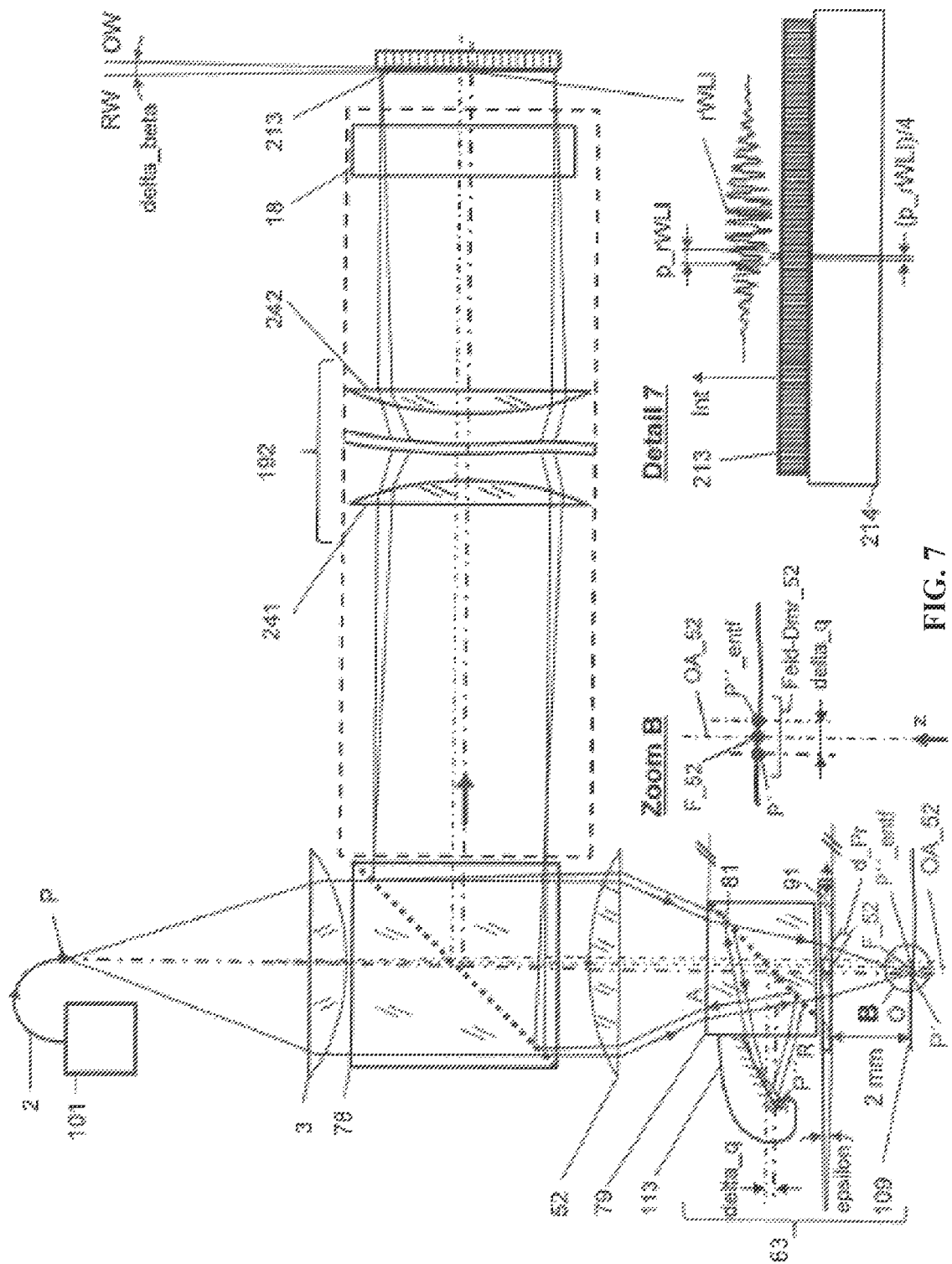
Figure 8:
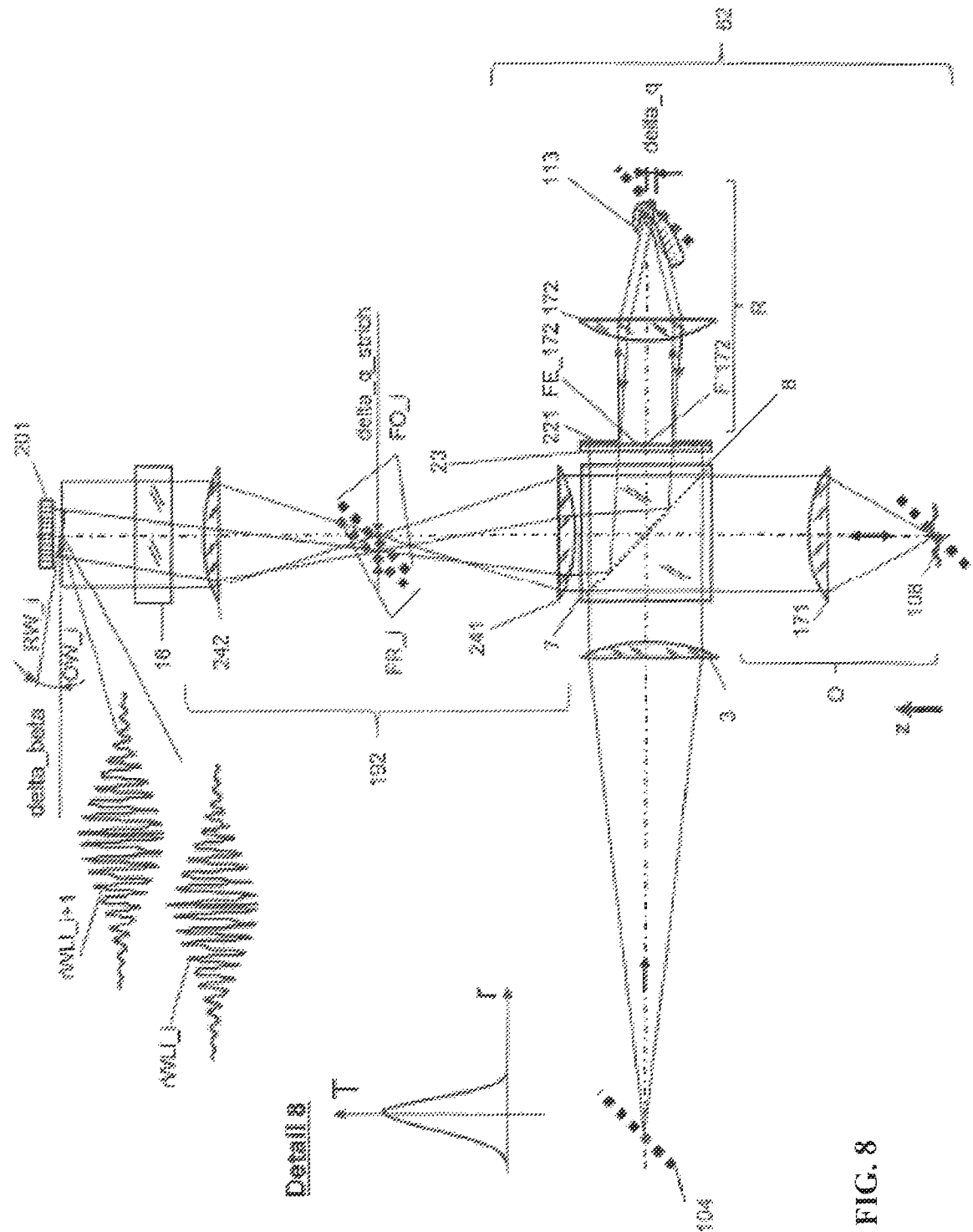
Figure 9:
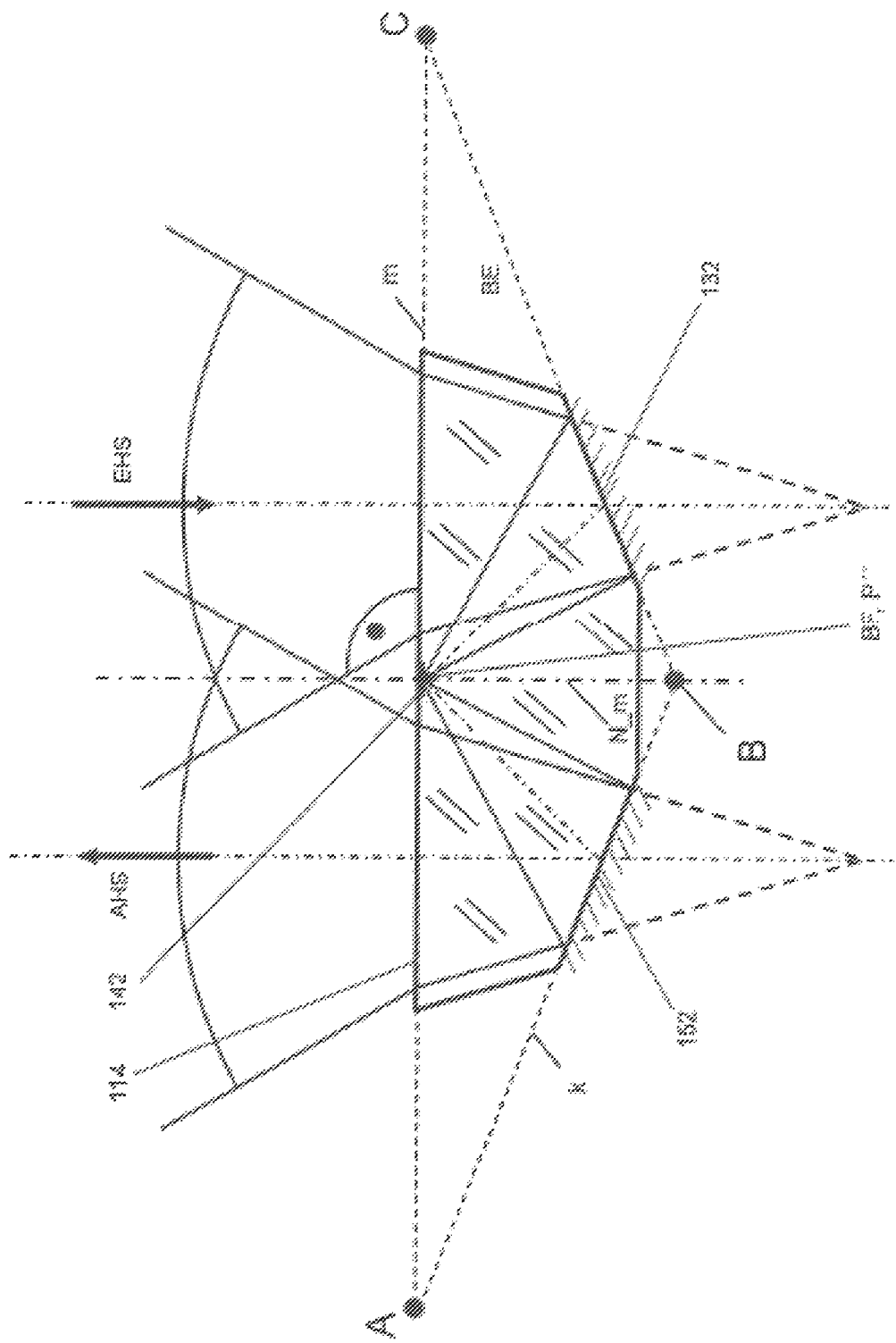
Figure 12:
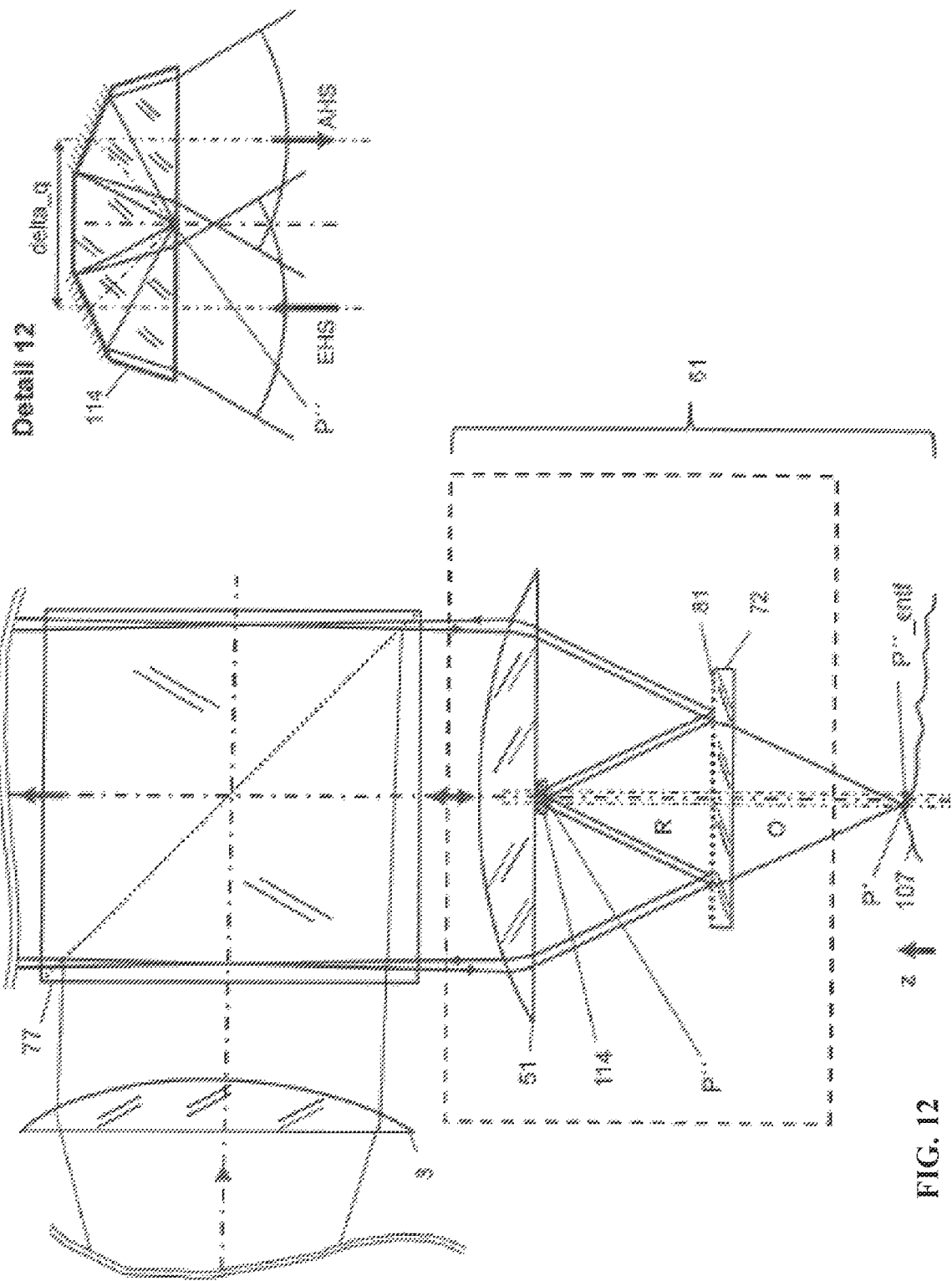
Figure 13:
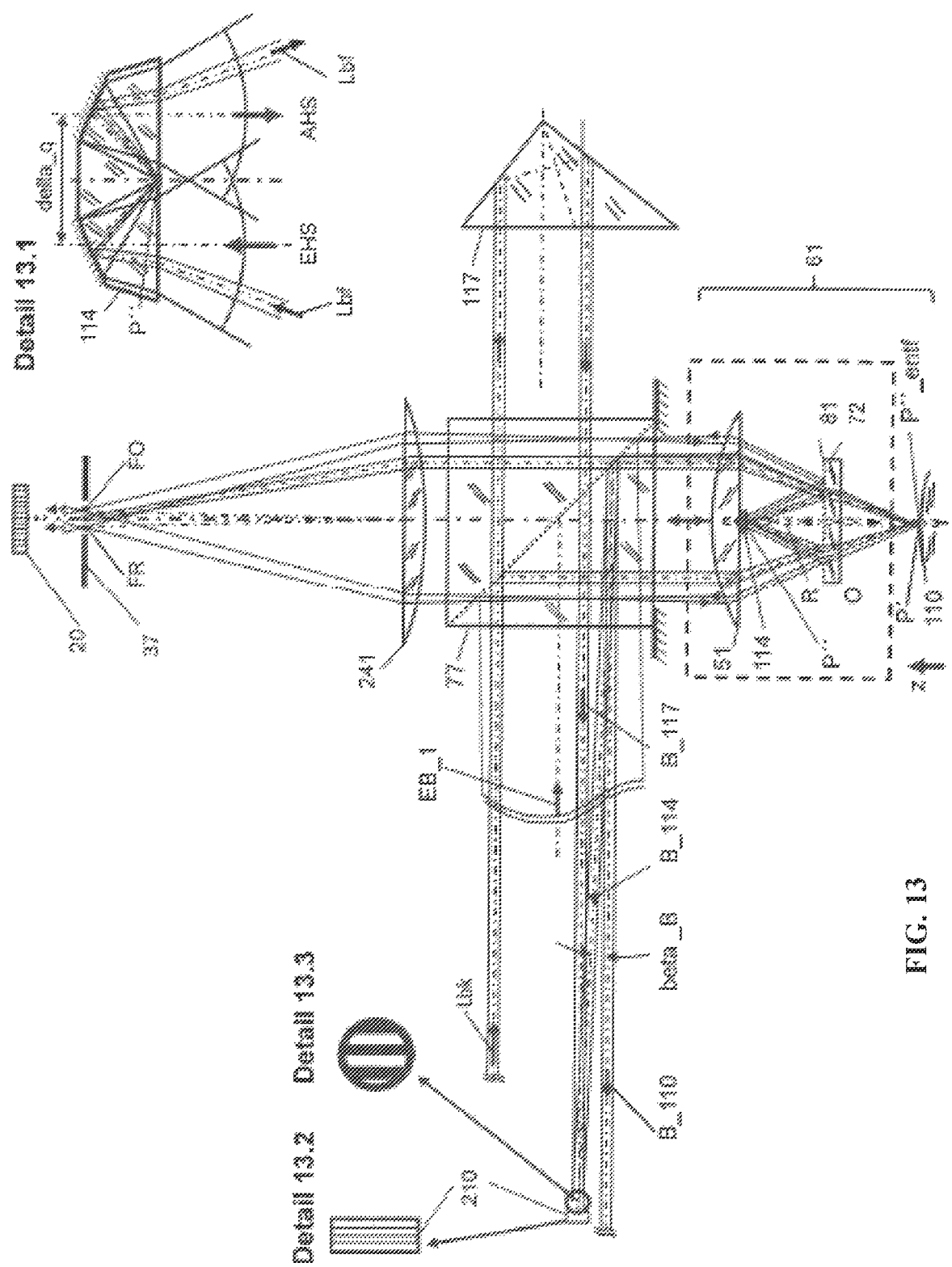
Figure 14:
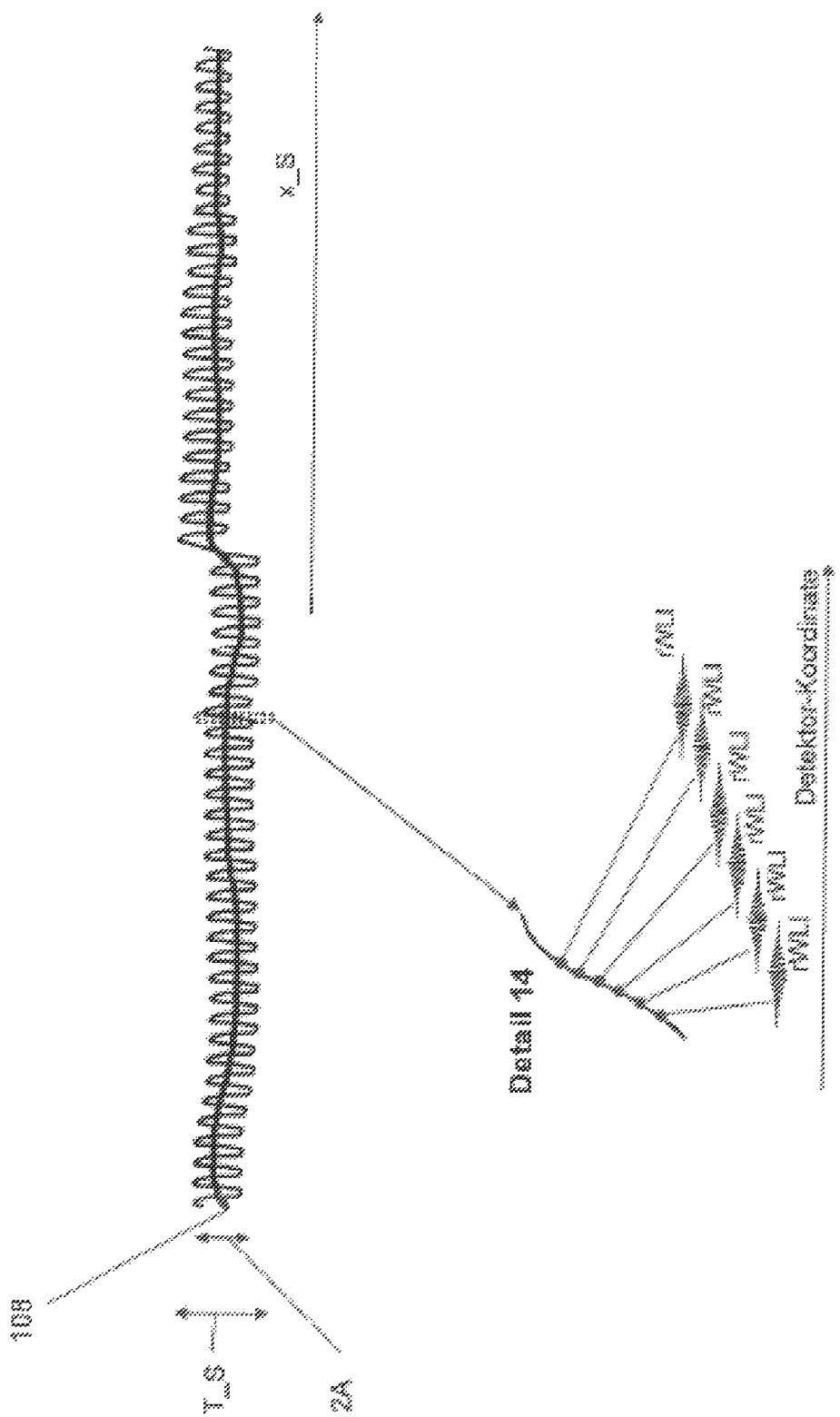

The invention will be described in the following by way of example with reference to FIGS. 1 to 14 and the 6 listed embodiments without figure. The figures show:

FIG. 1 a schematic representation of an exemplary interferometric arrangement for robust two-beam interferometry with a Michelson interferometer and a triple reflection arrangement designed as a three-reflecting-surfaces prism;

FIG. 2 a view of the three-reflecting surfaces prism in FIG. 1;

FIG. 2a the mounting position of the three-reflecting surfaces prism in FIG. 1;

FIG. 3 another exemplary three-reflecting surfaces prism with a beam crossing;

FIG. 4 a schematic representation of an exemplary interferometric arrangement for robust two-beam interferometry with a Mirau interferometer and a triple reflection arrangement formed as a three-reflecting surfaces prism;

FIG. 5 a schematic representation of an exemplary interferometric arrangement for robust two-beam interferometry with a Linnik interferometer, a triple reflection arrangement formed as a three-reflecting surfaces prism, and a chromatic-confocal measurement system;

FIG. 6 an exemplary triple reflection arrangement in air design;

FIG. 7 a schematic illustration of another exemplary interferometric arrangement for robust two-beam interferometry with a Michelson interferometer;

FIG. 8 a schematic illustration of another exemplary interferometric arrangement for robust two-beam interferometry with a Michelson interferometer;

FIG. 9 an exemplary three-reflecting surfaces prism with a W-beam path;

FIG. 10 a schematic diagram of an exemplary interferometric arrangement for robust two-beam interferometry with a Linnik interferometer and with the three-reflecting surfaces prism shown in FIG. 9;

FIG. 11 exemplary spatial interferograms;

FIG. 12 a schematic illustration of an exemplary interferometric arrangement with a Mirau interferometer and with the three-reflecting surfaces prism shown in FIG. 9;

FIG. 13 an exemplary laser interferometer for optical scanning or sensing of a three-reflecting surfaces prism;

FIG. 14 an exemplary measurement of surface profiles and waviness, the profile depth of which exceeds that of the wave-optical depth of field of the interferometric sensor arrangement.

In the figures, like reference numerals are used for the same or similar elements. Furthermore, the term light is always used as a synonym for electromagnetic radiation from the terahertz, over the infrared to the deep UV spectrum.

FIG. 1 shows an exemplary interferometric arrangement for single-shot measurement. This arrangement is particularly suitable for waviness measurement on thin glass or measurement of the flatness or evenness deviation on polished silicon wafers, since they each have an optically smooth surface and thus directional reflection without speckle effects exists. The near-infrared light emanating from the fiber-coupled point light source 1 passes via the single-mode fiber 2 into the collimator 3, which is already part of the sensor head 4. The sensor head 4 further comprises a Michelson interferometer 6, an output imaging stage 16, a detector and optionally further optical elements. The sensor head 4 is designed to be movable in the z direction and formed in a precision-guided manner for highly dynamic refocusing. The point light source 1 may e.g. include three superluminescent diodes to operate the interferometric arrangement in the spectral range from 750 nm to 950 nm. The point light source 1 may also be another point light source, e.g. a frequency comb laser with a micro cavity.

The imaging stage for the point light source 1 represents a chromatically fully corrected optical system from the end of the fiber 2 to the measurement object 10, which here comprises thin glass of 30 µm thickness. The glass path lengths and the glass dispersion of the 112° beam splitter arrangement 7, the glass wedge 91 and the three-reflecting surfaces prism 111 are exactly compensated by the slidable and then fixable glass wedge 91. For this purpose, the wedge angle epsilon of the glass wedge 91 is at least approximately incorporated into the 112° beam splitter arrangement 7, so that a plane parallel plate effectively exists in the imaging beam path and thus there is no spectral splitting in the imaging stage.

This glass wedge 91 is aligned perpendicular to the optical axis in front of the microscope objective and also has a protective function. In FIG. 1, the thickness of the glass wedge 91 in the middle is about 1.6 mm, in the edge regions about 1.3 mm and 1.9 mm, so that a very good balance of the optical path lengths in the interferometer 6 can be set. Thus, the white light interferogram has at least approximately the phase zero at the centroid of the envelope. The adjusted glass wedge 91 and the three-reflecting surfaces prism 111 are made of the same low-dispersive glass material. After adjustment, the two interferometer arms have the same glass path lengths for the respective main ray, resulting in a symmetrical white light interferogram. The light reflected on the thin glass 10 passes back through the glass wedge 91 into the 112° beam splitter arrangement 7.

In the reference arm of the Michelson interferometer 6, a three-reflecting surfaces prism 111 with a crossed beam path is arranged as the end reflector. FIGS. 2 and 2a show schematically the structure of the three-reflecting surfaces prism 111 (FIG. 2) and its mounting position (FIG. 2a) in the interferometer.

The three-reflecting surfaces prism 111 has a (beam) input surface 12 and three reflecting surfaces 13, 14 and 15. The three reflecting surfaces 13, 14 and 15 are each at least approximately perpendicular to a common reference plane BE. The reflecting surfaces 13, 14 and 15 are formed as planar mirrors. The three track lines of the planes, which are represented by the three reflecting surfaces, form a triangle ABC with an obtuse angle in the reference plane BE.

The reflecting surface 13 includes the points B and C and is used as the first or third surface (in the order of reflections) for reflection of the beam. The reflecting surface 14 lies on an extended straight line m, which includes the points A and C, and is used as the second surface (in the order of reflections) for reflection of the beam. The angle between the reflecting surfaces 13 and 14 is an acute angle. The reflecting surface 15 lies on an extended straight line k, which includes the points A and B. The reflecting surface 14 and the reflecting surface 15 form an obtuse angle CBD.

Furthermore, a normal N_m runs on the second reflecting surface through the point B. The beam focus BF lies at least approximately on the normal N_m and at least approximately in the vicinity of the reflecting surface 14.

The three-reflecting surfaces prism 111 is designed for a maximum numerical aperture N.A.=0.2, which is not fully exploited here in FIG. 1. By a geometric design of the three-reflecting surfaces prism 111, a transverse offset of the beam delta_q=500 µm is given. The microscope objective 5 has a focal length f'S=40 mm and a numerical aperture N.A.=0.09, which is fully exploited, so that the numerical aperture for the focused beam is N.A.=0.09. Thus, the pupil diameter is specified with d_P 7.2 mm. In the pupil plane, a maximum optical path difference OPD_max of delta_q* (d_P/f'5) results. In the present example, OPD_max=delta_q*(d_P/f'5)=500 µm*(7.2 mm/40 mm)=90 µm. For a centroid wavelength of 850 nm, there are thus about 106 interference fringes, which can be well detected with a line scan camera 20 with 1024 pixels and 7 mm length, wherein due to the shape of the envelope of the WLI wavelet (WLI: white light interferogram), given by the light spectrum of the interfering wavefronts, only clearly less than 100 periods in the WLI wavelet can be detected. The 112° beam splitter arrangement 7 according to FIG. 1 also permits the use of microscope objectives with a significantly shorter focal length than 40 mm, without resulting in problems with the free space for the components of the detection beam path at the output of the interferometer 6.

In a 112° beam splitter assembly 7 with 12 mm edge length and a thickness d_Pr of the glass wedge 91 of 1.6 mm, which in total corresponds to a cover glass correction of 13.6 mm, a free working distance of at least 15 mm results for the microscope objective 5 with a focal length of 40 mm, even if the image-side main plane in the microscope objective 5 is located slightly behind the front lens. At the output of the interferometer 6, an output imaging stage 16 is arranged. It represents a chromatically well-corrected overall optical system from the output of the interferometer 6 to the detector 20. The cylinder optics 18 contained therein (see also detail 1) serves for linear compression of the beam to the fast line scan camera 20, which receives the interference light by an output beam splitter plate 19. The transmitted interference light reaches the fast photodiode detectors 211 and 212. The fast photodiode detector 211 arranged on the left side of the field and the fast photodiode detector 212 arranged on the right side of the field are used to detect the focus position of the sensor head 4 with the interferometer 6. By the photodiode detectors 211 and 212, the respective width of which corresponds to about a quarter of the period in the WLI wavelet, a local amplitude A of the white light interferogram can be determined in a known manner at least approximately according to the following formula from 5 photodiode elements, which supply the signal values I1, I2, I3, I4 and I5.

$$A = \sqrt{(I_1 - 2I_3 + I_5)^2 + (2I_2 - 2I_4)^2}$$  Equation (1)

The determination of the local amplitude values A of the white light interferogram is performed several times on each of the two sides of the field, and thus the difference signal of the sums of the determined local amplitude values is formed for the left and the right sides by a digital signal processor 216, wherein the amplitude values are always represented by a positive value. Depending on which of the two sides predominates in the sum signal, i.e. a positive or negative difference exists, the sensor head with interferometer 6 is readjusted to the thin glass surface 10 at depth by a highly dynamic piezo actuator system 218. This balance method is a well-known method for control systems to one of ordinary skill in the art.

Other equations for determining or estimating the local signal amplitudes A of a white light interferogram are also known and also applicable, which are based, for example, only on the difference of directly adjacent intensity values in the spatial interferogram. The calculation of the signal amplitudes A can be carried out extremely quickly by the digital signal processor 216, which is assigned to the photodiode detector and which accesses the signals of the sensor elements of the photodiodes in parallel. By evaluating the amplitudes of a plurality of oscillations under the envelope of the spatial interferogram, it is possible to prevent a faulty signal from arising when the envelope deviates from the Gaussian distribution curve, for example when the envelope is modulated.

The comparatively large spectral bandwidth of the light source 1 of about 200 nm causes a comparatively short coherence length. The arrangement of FIG. 1 is thus particularly suitable for thin glass measurements. In addition, the arrangement according to FIG. 1 can also be used for measuring the shape of polished aspheres, including progressive lenses, also of plastic. When progressive lenses are measured, the arrangement of FIG. 1 may be part of a multi-coordinate ultra-precision measuring machine. This machine is, among others, constructed with an ultra-precise tilting device, also with a tilt angle sensor, so that always an at least approximately perpendicular measurement of the object surface can be performed.

The arrangement according to FIG. 1 also permits the measurement of the layer thickness of thin glass 10 with the thickness of, for example, 30 µm. In this case, two clearly separated spatial white light interferograms are to be evaluated. Thus, both the waviness and the thickness of the thin glass 10 with a depth resolution in the single-digit nanometer range can be measured simultaneously.

In a first embodiment (1) without a figure, the determination of a local amplitude A of the WLI wavelet on both the right side and on the left side of the optical axis in the field can be carried out with a quadruple photodiode in each case. Here, the pitch of the quadruple photodiodes is each one quarter of the known mean WLI wavelet period length. The evaluation can be done by a special processor. However, this requires a symmetric-form envelope free of local modulations. The quadruple photodiodes receive the WLI light by decoupling through a beam splitter. Thus, an extremely fast comparison of left and right amplitudes of the spatial interferogram is done at a fixed location in order to generate a defocus signal for depth control.

The prism arrangement 111 in FIG. 2, with three reflections and a crossing point K, is e.g. used if a small lateral offset delta_q is to be achieved. This can be advantageous for a Michelson, a Linnik or even a Mirau interferometer, in particular if the focal length of the microscope objectives is low. This configuration has a small optical path length relative to the lateral offset delta_q. In the glass of the prism arrangement 111, a half opening angle of 9° is achieved. Here, linearly polarized light is preferably used.

FIG. 3 likewise shows an exemplary prism arrangement with three reflections, i.e. a three-reflecting surfaces prism 112, with a beam crossing and a crossing point K of the input beam and the output beam and the virtual mirror plane VSE. This special prism arrangement is used if a comparatively high numerical aperture N.A. is to be achieved for the focused beam. The three-reflecting surfaces prism 112 is used in arrangements according to FIGS. 4 and 5. FIG. 3 is about the maximization of the N.A. For 15.35°, a N.A. of 0.4 for the glass type BK7 is achieved. Higher-refractive glasses allow an even higher N.A. of values up to 0.5. The angle gamma here is about 0° (degrees). This is a prerequisite for achieving a comparatively high N.A. However, the variant with a half aperture angle of 15° (degrees) shown here leads to a comparatively large construction volume of the prism.

In the following, the features of the three-reflecting surfaces prism 112 are listed. The three-reflecting surfaces prism 112 has three reflecting surfaces 13, 14 and 15, the arrangement of which is similar to the arrangement of the reflecting surfaces of the three-reflecting surfaces prism 111. For a maximum N.A., the normal N_m of the reflecting surface 14, which includes the straight line m, hits the edge of the two other reflecting surfaces 13 and 15 in point B. There is an obtuse angle. A marginal ray propagates approximately parallel to surface 14. The beam focus BF is at least approximately on the surface 14. The angle BAC and the angle BCE are less than 90° (degrees) and the angle CBD is more than 90° (degrees). The straight line m, which includes the distance AC, and a marginal ray RS in the prism enclose an angle gamma of less than 5° (degrees), for example, 0°. The straight line m and a marginal ray RS in the prism preferably enclose an angle smaller than 1° (degree). The signed angle tau between the input main ray EHS and the reflecting surface 14 is preferably less than −1° (degrees), e.g. between −2° (degrees) and −16° (degrees). From a manufacturing point of view, a lateral offset delta_q of 0.2 mm is still easy to realize. The half aperture angle Alpha_p of the three-reflecting surfaces prism 111 is ±15° in this example.

The three-reflecting surfaces prism 112 can be easily combined with a microscope objective of the magnification 20× and the N.A.=0.4 as a reference reflector. This is done in conjunction with a Michelson interferometer in a second embodiment (2) without figure. For this purpose, linearly polarized light with a perpendicular polarization direction is used.

FIG. 4 illustrates a Mirau interferometer arrangement for measuring a precision-machined metal object 107 having a three-reflecting surfaces prism 112 with a beam crossing. The three-reflecting surfaces prism 112 is cemented onto the front lens of the microscope objective 51. The microscope objective 51 has a focal length f'=7 mm and a numerical aperture N.A.=0.5. The free working distance to the metal object 107 is 1.5 mm. The Mirau interferometer arrangement is designed to be movable in the z-direction for the purpose of focusing.

In order to reduce dispersion effects, the beam splitter substrate 72, which is well-matched in its thickness of 1.3 mm to the glass path of the three-reflecting surfaces prism 112, is preferably made of the same material as the three-reflecting surfaces prism 112. This leads to a balanced interferometer. In the object space, an off-axis measurement point P' is shown, and in the reference arm a reference point P" is shown. The position of the developed coherent reference point P"_entf is also off-axis and the point P"_entf is at the same distance from the optical axis of the microscope objective 51 as the measurement point P'. The given symmetry position in the field reduces error influences. With this arrangement, the spatial interferogram in the pupil is compressed by cylinder optics in the transfer stage, so that the center in the pupil, which here is missing due to shading, does not present a problem. The detail 4 shows the three-reflecting surfaces prism 112 in the installation position in enlarged scale.

FIG. 5 shows an exemplary interferometric arrangement with a Linnik interferometer for a measurement point and with a three-reflecting surfaces prism 112 as well as a chromatic-confocal measuring system on a coarser scale, the beam path of which is arranged coaxially with the object beam path in the object arm O of the interferometer. In a Linnik interferometer, there is no shading in the pupil, which is an advantage. The high-aperture measuring microscope objective 171 in the beam path of the Linnik interferometer has a focal length of 7 mm. The N.A. is 0.65 and the transverse offset is delta_q=200 µm. On the front lens of the reference objective 172, an optically thin apodization filter 222 with radially symmetrical Gaussian characteristics is arranged. The apodization filter 222 allows reducing the reference beam spherical wave in the N.A. significantly without causing more powerful harmful diffraction effects, so that the resulting N.A. then fits the much smaller N.A. of about 0.48 of the three-reflecting surfaces prism 112 with cross-beam path. However, the smaller N.A. does not present a problem, since spatial interferograms are only evaluated in the middle of the pupil. Detail 5 shows the enlarged three-reflecting surfaces prism 112 in the installation position. Furthermore, an observation system for the objective 108 with a light source 35 and a fast matrix camera 209 is arranged, the beam path of which is linked via the color splitter cubes 74 and 73. In addition, a chromatic-confocal measuring system for obtaining a focus signal is arranged, which is constructed with a light source 31 and a detector 38 that is composed of a 100 kHz line camera with an upstream spectrometer for a light spot in the wavelength range from 580 nm to 700 nm.

FIG. 6 shows a three-reflecting surfaces arrangement 113 (triple reflection arrangement) in air design with a crossed beam path with a crossing point K. This arrangement is used if a particularly small offset delta_q is to be achieved. The arrangement can be produced as a metal joining group, for example. This arrangement may be advantageous for a Linnik, a Mirau or a Michelson interferometer as a reference reflector. For example, the three-reflecting surfaces arrangement 113 can be used as a reference reflector (end reflector in the reference beam path) in FIGS. 1, 4 and 5. Preferably, linearly polarized light is used.

FIG. 7 shows a further exemplary interferometric arrangement with a Michelson interferometer. The light emanating from a fiber-coupled point light source 101 with a plurality of double superluminescent diodes in the spectral range from 490 nm to 680 nm passes through the collimator 3 and passes through the coupling and decoupling beam splitter cube 78 via an objective 52 (e.g. of the type 20× objective G Plan APO from the company Mitutuo with the focal length f'=10 mm and the N.A.=0.28) into the Michelson interferometer 63. The focused light hits the splitter cube 71 with 3.5 mm edge length, which corresponds to the cover glass correction of this objective. This yields a 2 mm free working distance to the measurement object 109, which e.g. represents an aluminum surface in the transition region between optically smooth and rough. The three-reflecting surfaces arrangement (triple reflection arrangement) 113 in air design with a crossed radiation path with the crossing point K is constructed with a transverse offset delta_q of 300 µm. Zoom B shows the symmetrical use of the field of the objective 52, since the points P' and P"_entf are located approximately equidistant from the focal point F_52 of the objective 52. Due to the comparatively small numerical aperture, this arrangement is rather not to be used for measuring the roughness. This is about the profile measurement. For this purpose, a very fast multiple photodiode detector 213 with a hardware processor 214 is used in order to determine the position of the centroid of a white light interferogram in the sub-millisecond range. In order to enable a numerically simple evaluation, the period length p_rWLI of an oscillation in the spatial interferogram is four times the pitch of the diodes in the multiple photodiode detector 213, which is shown in detail 7. This can be well observed due to the factually invariant angle between the interfering wavefronts RW and OW in the detection delta beta.

FIG. 8 shows an exemplary interferometric arrangement with a Linnik interferometer 62 with a multipoint light source 104 constructed of several superluminescent diodes, and with a microscope objective 171 in the object arm O of the interferometer 62. The microscope objective 171 has a numerical Aperture N.A.=0.5 and a focal length of 6 mm. The object 108 has a rough surface. In the reference beam path R of the interferometer 62 there is arranged a reference microscope objective 172 with a numerical aperture N.A. of 0.28 and a three-reflection arrangement 113 according to FIG. 6 with a crossed beam path, the transverse offset of which is delta_q=250 µm. A variety of measurement points are measured. In order to adapt the three-reflection arrangement 113 with the numerical aperture, which is smaller toward the object beam path, an optically thin apodization filter 221 with a radially symmetric Gaussian characteristic is arranged on a substrate 23 in the Fourier plane FE_172 of the reference objective 172. The Gaussian characteristic of the apodization filter 221 is shown in detail 8. The apodization filter 221 reduces the reference beam in N.A., making it N.A. of 0.28 of the three-reflection arrangement 113. After combining the interfering beams of reference and object beam paths by the beam splitter cube 7, they pass through the optical 4f-transfer stage 192, consisting of lens barrel objective 241 and camera objective 241, and the cylinder optics 18. Each measurement point optically measurable in the object beam path generates a white light Interferogram on the matrix camera 201, so that a plurality of adjacent spatial white light interferograms (rWLI_i, where i is an integer) can be detected with the same spatial frequency. In a further embodiment (3) without figure, it is also possible to use a 4f-transfer stage, not shown here, in the two interferometer arms each. This is advantageous if the Fourier plane of the objective 172 is geometrically inaccessible due to the objective design. Thus, the apodization filter can be arranged in a plane that is optically conjugate to the Fourier plane FE_172 of the reference objective 172.

FIG. 9 shows a W-type three-reflecting surfaces prism 114 (i.e., with a W beam path) in the reference arm of a two-beam interferometer, wherein the prism allows a large numerical aperture of up to 0.8 for the beam path in the reference arm. The three optically effective surfaces 132, 142 and 152 (i.e., reflecting surfaces) of the W-type three-reflection surfaces prism 114 are each at least approximately perpendicular to a common reference plane BE. The reflecting surfaces 132, 142 and 152 may be formed as a plane mirror. The three track lines of the planes, which are represented by the three reflecting surfaces 132, 142 and 152, form a triangle ABC with an obtuse angle in the reference plane BE. In the illustrated example, the reflecting surface 132 lies on an (extended) straight line connecting points C and B, the reflecting surface 142 lies on an (extended) straight line m, on which points A and C are located, and the reflecting surface 152 lies on an (extended) straight line k, on which points A and B are located. The reflecting surface 142 and the reflecting surface 132 are disposed at an acute angle relative to each other (i.e., the angle between the straight lines l and m is an acute angle). The reflecting surface 132 and the reflecting surface 152 are disposed at an obtuse angle relative to each other (i.e., the angle between the straight lines k and l is an obtuse angle). The reflecting surface 142 is used as the second of the three reflecting surfaces for reflection of a focused beam FB, the reflecting surface 132 is used as the first or third of the three reflecting surfaces for reflection.

The three-reflecting surfaces prism 114 produces a transverse offset of the amount delta_q for the reference beam, which is particularly large in relation to the lateral extent of this prism. A special feature here is that the normal N_m from point B, perpendicular to the reflecting surface 142, which includes the distance AC, at least approximately hits the point B. The three-reflecting surfaces prism 114 is used in the same manner as a triple-reflection arrangement with a crossed beam path with a crossing point K. In a further embodiment (4) without figure, a triple-reflection arrangement is formed with a prism having two mirror surfaces and a total reflecting surface including the straight line m. It is only important that always three reflections occur or that an odd number of reflections occur in the reference beam path. The two-beam interferometer according to FIG. 9 used for a W-type three-reflecting surfaces prism 114 may be a Michelson, a Mirau or a Linnik interferometer. The path length of the refractive material of this three-reflecting surfaces prism 114 is introduced in the object arm for compensation. In a further embodiment (5) without figure, the three-reflecting surfaces prism 114 may also be formed somewhat elongated to allow multiple measurement points along a line or a line as a reference light.

FIG. 10 illustrates a Linnik interferometer with a W-type three-reflecting surfaces prism 114 for a measurement point. Detail 10 shows the three-reflecting surfaces prism 114 in the installation position. Downstream of the fiber-coupled point light source 1 there is arranged a fiber-based microresonator 39, designed as a Fabry-Perot interferometer, with one time the optical path length L of the resonator, which is slightly above 10 µm. There are also pulses that are delayed by 2L. Thus, a coherence function is given with recurring maxima and white light interferences can occur even at a path difference of 2L. This is shown in FIG. 11. These white light interferences are detected by a fast matrix camera 202. FIG. 11 shows three exemplary short-coherence spatial interferograms rWLIi, where i=0, +1 and −1.

The microscope objectives 171 and 172 have a focal length of 4 mm and a numerical aperture of N.A.=0.8. The transverse offset is delta_q=150 µm. Here as well, as in the arrangement according to FIG. 5, an observation system for the object 108 with a light source 35 and a fast matrix camera 209 is arranged, the beam path of which is linked via the color splitter cubes 74 and 73. And here, too, a chromatic-confocal measuring system for obtaining a focus signal is arranged, which is constructed with a light source 31 and a detector 38 that is composed of a 100 KHz line camera with an upstream spectrometer for a light spot. In a further embodiment (6) without figure, a frequency comb laser with microresonator is used as the light source.

FIG. 12 illustrates a Mirau interferometer with a W-type three-reflecting surfaces prism 114 for a measurement point. The focal length of the microscope objective 51 for the Mirau interferometer is 7 mm and the numerical aperture N.A.=0.65 and the transverse offset delta_q=200 µm. Here, too, a chromatic-confocal measuring system is used in a coarser scale according to FIG. 5 for focus position control, the beam path of which is arranged coaxially to the object beam path in the object arm O of the interferometer. There is a missing area for the Mirau interferometer due to shading due to the reflection prism in the pupil. Therefore, cylinder optics 18 are arranged in the outgoing beam path of the Mirau interferometer, which focus on a line-like/narrow area on the detector. Detail 12 shows the enlarged W-type three-reflecting surfaces prism 114 in the installation position.

FIG. 13 shows a laser interferometer 41 for optical scanning of the three-reflecting surfaces prism 114, which is located in the Mirau objective 61 in order to be able to measure a movement of the Mirau objective 61 in the z direction with maximum accuracy.

The advantage of using a three-reflecting surfaces prism 114 is that the angle beta_B between the 114 and 110 beams permits a very simple geometric decoupling from the laser light of the beam B_110, which is reflected directly at the object 110—even if it is reflective. The laser light reflected by the object 110, here an optically polished surface—in the form of the beam B_110—is thus kept away from the quadruple photodiode detector 210 in order to avoid interfering interferences. Detail 13.1 shows the enlarged W-type three-reflecting surfaces prism 114 in the installation position. Detail 13.2 illustrates the photodiode block 210 and detail 13.3 illustrates the interferences of the interfering laser beams formed there.

FIG. 14 shows a possibility of measuring profile and waviness on surfaces whose profile depth exceeds that of the wave-optical depth of field of the interferometric sensor arrangement. The sensor arrangement is moved in the z-direction in a vibrating manner and thereby adaptively readjusted to the surface waves and also steps in the object surface by a coaxial chromatic confocal sensor system, cf. FIG. 5. By reading a fast line camera, spatial white light interferograms rWLI can be detected. The displacement in the z-direction is permanently measured and calculated by the laser interferometer 41 in high-resolution.

Detail 14 shows, in zoom, measurement points on a flank and the white light interferograms rWLI shifting laterally in the detector plane in a depth scan. The intensity wavelets are shown slightly offset in height for reasons of better presentability.

In principle, the arrangements described above can be realized with all two-beam interferometers. The arrangements with a Mirau interferometer, however, may be subject to certain technical limitations, since shading may occur in the pupil surface. By introducing moderate asymmetries in the Mirau interferometer system—in the optical path lengths—however, as described above, at least one-sided detection of the short-coherence interferogram can take place. The arrangements with a Michelson or a Linnik interferometer are free of these limitations.

The arrangements and methods described above are suitable for detecting distance, profile, shape, waviness, roughness or optical path length in or on optically rough or smooth objects and/or for optical coherence tomography (OCT). For example, the above described arrangements and methods can be used for measurements on tensioned machine surfaces with high lateral and high depth resolutions in the manufacturing process or in a close-to-manufacturing environment. Furthermore, robust 3D detection using single-shot interferometry with a comparatively high numerical aperture (up to, for example, N.A.=0.8 in extreme cases, typically between 0.25 and 0.55) is possible with a high refractive index of the components. A high numerical aperture serves for better lateral resolution in order to be able to conduct measurements on tensioned machine surfaces with high lateral and high-depth resolutions, as well as for better light output.

| List of reference numerals | |
|---|---|
| Reference no. | Designation |
| 1 | Light source, e.g. fiber-coupled point light source with three double superluminescent diodes to operate the light source in the spectral range from 750 nm to 950 nm for interferometric use |
| 101 | Light source, e.g. fiber-coupled point light source with multiple double superluminescent diodes to operate the light source in the spectral range from 490 nm to 680 nm for interferometric use |
| 103 | Light source for areal illumination of the measurement object, e.g. for capture by a matrix camera |
| 104 | Line light source, e.g. composed of several superluminescent diodes |
| 2 | Single-mode fiber |
| 3 | Collimator |
| 4 | Sensor head, preferably precision-guided in a movable manner in z-direction for highly dynamic refocusing |
| 5 | Microscope objective, preferably with a focal length f' = 40 mm, a numerical aperture N.A. = 0.09 and with a pupil diameter d_P in the Fourier plane of 7.2 mm |
| 51 | Microscope-objektive for Mirau interferometer |
| 52 | Microscope objective, e.g. 20× Mitutuo objective G Plan APO with a focal length f = 10 mm, a numerical aperture NA = 0.28, a corrected glass path length of 3.5 mm and an object field diameter of 0.55 mm, for which a transverse offset delta_q = 0.3 mm fits well |
| 6 | Michelson interferometer, uses output B |
| 61 | Mirau interferometer |
| 62 | Linnik interferometer |
| 63 | Michelson interferometer, uses output A |
| 7 | Beam splitter arrangement, e.g. 112° beam splitter arrangement |
| 71 | 90° beam splitter cube in the Michelson interferometer 601 or Linnik interferometer 62 |
| 72 | Substrate for beam splitter |
| 73 | Coupling and decoupling beam splitter cube, which preferably transmits light above 750 nm wavelength and reflects light below 720 nm |

| List of reference numerals | |
|---|---|
| Reference no. | Designation |
| 74 | Color beam splitter for coupling in and out of light for camera observation, preferably transmission above 560 nm, reflection below 560 nm |
| 75 | 50:50 Coupling and decoupling beam splitter cube for observation camera |
| 76 | 50:50 Coupling and decoupling beam splitter cube for chromatic-confocal sensors for focus position determination |
| 77 | 50:50 Coupling and decoupling beam splitter cube for Mirau interferometer 61 |
| 78 | 50:50 Coupling and decoupling beam splitter cube for Michelson interferometer 63 |
| 79 | 50:50 beam splitter cube, e.g. with 3.5 mm edge length in the Michelson interferometer 63 |
| 8 | 50:50 beam splitter layer |
| 81 | Beam splitter layer, e.g. with 80% transmission and 20% reflection |
| 91 | Glass wedge<br>This glass wedge corresponds to a compensation plate with regard to its optical effect. This glass wedge is aligned with its outside perpendicular to the optical axis of the microscope objective. This glass wedge also has a protective function. In FIG. 1, its thickness in the middle is between 1.4 mm and 1.7 mm, depending on the state of adjustment. |
| 93 | Compensating plate in a Linnik interferometer 62. This compensation plate is matched to the glass path length of the three-reflecting surfaces prism 112 in terms of the glass path length. |
| 94 | Mechanical protection angle |
| 10 | Thin glass as a measurement object with a thickness of 300 μm |
| 107 | Precision-machined metal object |
| 108 | Measuring object with rough surface |
| 109 | Aluminum surface in the transition region between optically smooth and rough |
| 110 | Optically polished surface |
| 111 | Three-reflecting surfaces prism with crossed beam path with crossing point K with a lateral offset delta_q. In FIG. 1, delta_q = 0.5 mm and the optical path length is 1.6 mm. |
| 112 | Three-reflecting surfaces prism with crossed beam path with crossing point K and geometry for maximum numerical aperture |
| 113 | Triple reflection arrangement in air design with crossed beam path with crossing point K |
| 114 | W-type three-reflecting surfaces prism |
| 115 | Fixture components for three-reflecting surfaces prism 112 |
| 116 | Joining surfaces for three-reflecting surfaces arrangement in air design 113 |
| 117 | Tripel prism, room corner |
| 12 | Input surface of the three-reflecting surfaces prism with crossed beam path |
| 13 | First mirror surface of the three-reflecting surfaces prism 111 |
| 131 | First mirror surface of the triple reflection arrangement 112 in air design |
| 132 | First mirror surface of the W-type three-reflecting surfaces prism 114 |
| 14 | Second mirror surface of the three-reflecting surfaces prism 111 |
| 141 | Second mirror surface of the triple reflection arrangement 112 in air design |
| 142 | Second mirror surface of the W-type three-reflecting surfaces prism 114, e.g. designed as a micromirror |
| 15 | Third mirror surface of the three-reflecting surfaces prism 111 |
| 151 | Third mirror surface of the triple reflection arrangement 112 in air design |
| 152 | Third mirror surface of the W-type three-reflecting surfaces prism 114 |
| 16 | Output imaging stage<br>Chromatically fully corrected overall optical system 2 from the interferometer output to the detector |
| 17 | Objective at the output of the Michelson interferometer, f′ = 40 mm and N.A. = 0.09 in FIG. 1 |
| 171 | High-aperture measuring microscope objective in the beam path of a Linnik interferometer |
| 172 | High-aperture reference microscope objective in the beam path of a Linnik interferometer |
| 18 | Cylinder optics for compression of the beam on a fast line camera 20 |
| 19 | Decoupling beam splitter plate |
| 191 | Beam splitter layer on the decoupling beam splitter plate. The beam splitter layer preferably attenuates the "sidebands" in the spectrum to some extent in transmission, so that for the multiple photodiode detectors a WLI wavelet with a slightly wider weakly modulated envelope and on the fast line camera 20 a WLI wavelet with an envelope as narrow as possible arises. |

-continued

| List of reference numerals | |
|---|---|
| Reference no. | Designation |
| 192 | Optical 4f transfer stage, consisting of lens barrel objective 241 and camera objective 241 |
| 20 | Fast line camera with 1024 pixels, detects a spatial white light interferogram (rWLI) |
| 201 | Fast matrix camera, detects several white light interferograms (rWLI_i, where i is an integer) of several measurement points |
| 202 | Fast matrix camera, detects several white light interferograms (rWLI_i, where i is an integer) of one measurement point |
| 209 | (Fast) matrix camera, detects a measurement object |
| 210 | (Very fast) quadruple photodiode detector for laser interferometer 41 |
| 211 | Very fast multiple photodiode detector - on the left side of the field for detecting the left amplitude values in real time for defocus signal |
| 212 | Very fast multiple photodiode detector - on the right side of the field for detecting the left amplitude values in real time for defocus signal |
| 213 | (Very fast) multiple photodiode detector with hardware processor |
| 214 | Digital signal processor for calculating the center of Gravity (CG) and the location of the phase position zero at the gravitational center |
| 216 | Digital signal processor for calculating the difference of the sum signals of the oscillations of the rWLIs under the envelope of the left and right areas of the field |
| 217 | Fast electronic power amplifier |
| 218 | Highly dynamic piezo-actuator system for setting the depth position with integrated electronic power amplifier 217 |
| 219 | Highly dynamic measuring system for measuring the depth of the sensor head 4 that is movable in the z-direction |
| 221 | Thin film apodization filter in Fourier plane FE' 172 or in a plane optically conjugate to it |
| 222 | Optically thin apodization filter with radially symmetric Gaussian characteristic on the front lens of the reference microscope objective 172 This allows reducing the reference beam spherical wave significantly without causing more powerful harmful diffraction effects, so that the resulting reference beam spherical wave then fits the much smaller N.A. of about 0.48 of the prism triple reflection reference reflector. In contrast, the measuring objective 172 in the object beam path 0 has a N.A. of 0.8. However, this does not pose a problem since rWLIs are only evaluated in the middle of the pupil. |
| 23 | Substrate for the apodization filter 221 in the Fourier plane FE_172 |
| 241 | Lens barrel objective |
| 242 | Camera objective |
| 31 | Broadband point light source, preferably in the spectral range from 580 nm to 700 nm. Preferably, the broadband point light source t provides the measurement light for a chromatic-confocal point sensor |
| 33 | Hyperchromatic system for depth splitting of foci |
| 35 | Light source, e.g. emitting in the spectral range of 480 nm to 550 nm |
| 36 | Pinhole |
| 37 | Double pinhole aperture, blocks all beams except those for the rWLI |
| 38 | Detector made up of a 100 kHz line camera with an upstream spectrometer for a light spot in the wavelength range from 580 nm to 700 nm |
| 39 | Fiber-based microresonator, designed as a Fabry-Perot interferometer |
| 41 | Laser interferometer to measure movement of the sensor head in z-direction |
| A | Local amplitude value |
| AHS | Output main ray of the beam exiting the end reflector |
| alpha_P | Half the aperture angle in the glass of the prism 112 |
| b | Lateral distance between adjacent rWLI |
| beta _B | Angle between the reflected laser ray beam from the three-reflecting surfaces prism114 and object 110 |
| BF | Beam focus |
| BE | Reference plane |
| EB_1 | Input beam from light source 1 |
| EHS | Input main ray of the beam entering the end reflector |
| epsilon | Wedge angle of the glass wedge 91, which is preferably less than/equal to one degree |
| delta beta | Angle between the interfering wavefronts RW and OW during detection |
| delta_q | Transverse offset of the beam in the reference arm of an interferometer |
| d_P | Pupil diameter of the microscope objective 5 |
| d_Pr | Center thickness of the glass wedge 91 |
| EB_1 | Input beam coming from fiber-coupled point light source 1, behind collimator 3 |
| f5 | Focal length of the microscope objective 5 |
| F'52 | Focus of the microscope objective 52 |

-continued

List of reference numerals

| Reference no. | Designation |
|---|---|
| FE_5 | Fourier plane/focal plane of the microscope objective 5 |
| FE_172 | Fourier plane/focal plane of the microscope objective 172 |
| Feld-Dmr_52 | Field diameter of the 20× Mitutuo microscope objective 52, it is around 0.5 mm |
| FO | Focus of the object beam |
| FO_i | Foci of the object beams of the number i |
| FR | Focus of the reference beam |
| FR_i | Foci of the reference beams of the number i |
| gamma | Angle |
| k | Straight line |
| kappa | Angle between the optical axis of the object beam path in the interferometer 6 and the optical axis of the beam path at the output B of the interferometer 6 |
| IG | Interference area |
| L | One time the optical path length of the microresonator |
| Lbk | Laser beam collimated |
| Lbf | Laser beam focused |
| rWLI | Spatial short-coherence interferogram |
| rWLI_i | Spatial short-coherence interferograms of the number i |
| OPD | Optical path difference |
| N.A. | Numerical aperture |
| OW | Object wavefront, inclined to the reference wavefront RW |
| OW | Object wavefront |
| P | Light spot |
| P' | Image of the light point in the object arm |
| P'' | Image of the light point in the reference arm |
| P''_entf | Image of the optically conjugate luminous point P'' in the object space after development, which is coherent to P' |
| r | Radius of the apodization filter 18 |
| p_rWLI | Period length of an oscillation in the spatial interferogram (rWLI) |
| RAS | Edge ray of the focused bundle |
| RW | Reference wavefront, tilted to the object wavefront OW |
| T | Transmittance of an apodization filter 221 or 222 over the radius r |
| T_S | Depth measuring range of the WLI sensor arrangement, in particular in the form of a Mirau interferometer 61 |
| tau | Angle between input main ray EHS and mirror surface 14 |
| VSE | Virtual mirror plane |
| rWLI | Spatial white light interferogram |
| x_O | Feed direction of the object |
| x_S | Feed direction of the sensor arrangement |
| z_rWLI | Depth measurement value, which is calculated from the rWLI signal |

The invention claimed is:

1. An arrangement for robust two-beam interferometry, comprising:

a source of short-coherent electromagnetic radiation for illuminating an object, an interferometer with an object beam path, a reference beam path, and a measurement plane (ME) in the object beam path, wherein surface or volume elements of the object to be optically measured are at least approximately located; and at least one rasterized detector for detecting electromagnetic radiation in the form of at least one spatial interferogram, wherein:

at least one end reflector is arranged in the reference beam path of the interferometer as a reference reflector, wherein the end reflector is formed as a triple reflection arrangement with three reflecting surfaces, the three reflecting surfaces each being at least approximately perpendicular to a common reference plane; and wherein three track lines of the planes, which are represented by the three reflecting surfaces, form a triangle with an obtuse angle in the reference plane, wherein a first reflecting surface lies on a straight line on which a first point and a second point of the triangle lie, a second reflecting surface lies on a straight line on which a third point and the first point of the triangle lie, and a third reflecting surface lies on a straight line on which the second point and the third point of the triangle lie, characterized in that:

the beam path of the triple reflection arrangement is crossed, the second reflecting surface is used as the second of the three reflecting surfaces for reflection of a focused beam and the first reflecting surface is used as the first or third of the three reflecting surfaces for reflection, the first reflecting surface and the second reflecting surface are disposed at an acute angle relative to each other, the first reflecting surface and the third reflecting surface are disposed at an obtuse angle CBD relative to each other, there is a normal from the second point of the triangle to the second reflecting surface, and for the triple reflection arrangement there is an angle gamma between a marginal ray of an incoming or outgoing beam and the second reflecting surface, and the angle gamma is less than 12° (degrees).

2. The arrangement for robust two-beam interferometry according to claim 1, wherein the beam focus lies at least approximately on the normal and at least approximately in a vicinity of the second reflecting surface.

3. The arrangement for robust two-beam interferometry according to claim 1, wherein the triple reflection arrangement is formed as an air mirror group or as a prism mirror group.

4. The arrangement for robust two-beam interferometry according to claim 1, wherein the third reflecting surface used by the focused beam is formed to be three times as long as the second reflecting surface.

5. The arrangement for robust two-beam interferometry according to claim 1, wherein the triple reflection arrangement is formed with a signed angle tau smaller than −1°, wherein the angle tau is the angle between an input main ray of the incoming beam and the second reflecting surface.

6. The arrangement for robust two-beam interferometry according to claim 1, wherein the beam focus is at least approximately on the normal and at least approximately in a vicinity of the second reflecting surface.

7. The arrangement for robust two-beam interferometry according to claim 1, wherein the source is formed as a frequency comb laser with a micro-cavity.

8. The arrangement for robust two-beam interferometry according to claim 1, wherein there is at least one depth measuring system in the object measuring field for detecting the measuring object, which is arranged with its beam path at least approximately coaxial with an interferometric beam path.

9. The arrangement for robust two-beam interferometry according to claim 8, wherein the depth measuring system is formed chromatically-confocally.

10. The arrangement for robust two-beam interferometry according to claim 1, wherein the interferometer in a reference arm is assigned an attenuation filter with a maximum of transmission in the center of an attenuation filter for reducing an aperture angle of the reference beam.

11. The arrangement for robust two-beam interferometry according to claim 10, wherein:
the attenuation filter is formed with a radially symmetric Gaussian characteristic; or
the attenuation filter is formed with a one-dimensional characteristic.

12. The arrangement for robust two-beam interferometry according to claim 1, wherein on the third reflecting surface there is a grazing incidence at least for the marginal ray of a beam with an incidence angle of greater than 75°.

13. The arrangement for robust two-beam interferometry according to claim 1, wherein:
the interferometer and the detector are arranged within a sensor head; and
the sensor head is associated with a highly dynamic piezo actuator system with a high-resolution depth measuring system assigned to it.

14. The arrangement for robust two-beam interferometry according to claim 1, wherein
an angle kappa between an optical axis of the object beam path in the interferometer and an optical axis of the beam path at an output of the interferometer is between 960 and 140°.

15. The arrangement for robust two-beam interferometry according to claim 1, further comprising:
a slidable glass wedge.

16. The arrangement for robust two-beam interferometry according to claim 15, wherein the triple reflection arrangement is formed as a three-reflecting-surfaces prism; and wherein the center thickness of the glass wedge at least approximately corresponds to a glass path length of a three-reflecting-surfaces prism.

17. A method for robust two-beam interferometry for detecting distance, depth, profile, shape, waviness and/or roughness or optical path length in or on technical or biological objects, and/or for optical coherence tomography with formation of a spatial white light interferogram, comprising:
providing an arrangement for robust two-beam interferometry, the arrangement comprising:
a source of short-coherent electromagnetic radiation for illuminating the object,
an interferometer with an object beam path, a reference beam path, and a measurement plane in the object beam path, wherein surface or volume elements of the object to be optically measured are at least approximately located, and
at least one rasterized detector for detecting electromagnetic radiation in the form of at least one spatial interferogram, wherein:
at least one end reflector is arranged in the reference beam path of the interferometer as a reference reflector, wherein the end reflector is formed as a having three reflecting surfaces arrangement with three reflecting surfaces, the three reflecting surfaces each being at least approximately perpendicular to a common reference plane, characterized in that:
in the reference beam path, a reduction of an aperture angle of the reference beam is performed by an attenuation filter attenuation; and
wherein three track lines of the planes, which are represented by the three reflecting surfaces, form a triangle with an obtuse angle in the reference plane, wherein a first reflecting surface lies on a straight line on which a first point and a second point of the triangle lie, a second reflecting surface lies on a straight line on which a third point and the first point of the triangle lie, and a third reflecting surface lies on a straight line on which the second point and the third point of the triangle lie, characterized in that:
the beam path of the three reflecting surfaces arrangement is crossed,
the second reflecting surface is used as the second of the three reflecting surfaces for reflection of a focused beam and the first reflecting surface is used as the first or third of the three reflecting surfaces for reflection,
the first reflecting surface and the second reflecting surface are disposed at an acute angle relative to each other,
the first reflecting surface and the third reflecting surface are disposed at an obtuse angle CBD relative to each other,
there is a normal from the second point of the triangle to the second reflecting surface, and
for the three reflecting surfaces arrangement here is an angle gamma between a marginal ray of an incoming or outgoing beam and the second reflecting surface, and the angle gamma is less than 12° (degrees).

18. The method for robust two-beam interferometry according to claim 17, wherein the reduction of the aperture angle of the reference beam is performed with the attenuation filter placed at least approximately in the Fourier plane of an objective in the reference beam path of a Linnik interferometer.

19. The method for robust two-beam interferometry according to claim 17, further comprising:
forming a balance signal for the focus control of the interferometer,
wherein to form the balance signal, first and second amounts of intensities of adjacent photoelements of a photodiode detector or pixels of a rasterized detector, which are located to the left from the spatial white light interferogram and to the right from a reference point, are determined and summed up by an arithmetic unit, whereby a first sums and a second sum are obtained, and
wherein the first sum and the second sum are subtracted from one another and the balance signal is derived therefrom.

20. The method for robust two-beam interferometry according to claim 17, wherein the interferometer and the detector are arranged within a sensor head, and the sensor head is associated with electromechanical highly dynamic means for tracking of the sensor head, which maintains the sensor head at each cooperative measurement point in a wave-optical depth of field in measurement real time, and
wherein the measurement result is formed from adding the depth measurement value of a tracking depth measurement system and the depth measurement value, which is determined from the spatial white light interferogram.

21. A method for robust two-beam interferometry for detecting distance, depth, profile, shape, waviness and/or roughness or optical path length in or on technical or biological objects, and/or for optical coherence tomography with formation of a white light spatial interferogram, comprising:
providing an arrangement for robust two-beam interferometry, the arrangement comprising:
a source of short-coherent electromagnetic radiation for illuminating the object,
an interferometer with an object beam path, a reference beam path, and a measurement plane (ME) in the object beam path, wherein surface or volume elements of the object to be optically measured are at least approximately located; and
at least one rasterized detector for detecting electromagnetic radiation in the form of at least one spatial interferogram, wherein:
at least one end reflector is arranged in the reference beam path of the interferometer as a reference reflector, wherein the end reflector is formed as a triple reflection arrangement with three reflecting surfaces, the three reflecting surfaces each being at least approximately perpendicular to a common reference plane, characterized in that:
a second optical scanning of the end reflector is performed by a second separate interferometer with a laser light source in order to be able to measure a displacement in a z direction of the interferometer belonging to the end reflector, which is rigidly connected to the end reflector; and
wherein three track lines of the planes, which are represented by the three reflecting surfaces, form a triangle with an obtuse angle in the reference plane, wherein a first reflecting surface lies on a straight line on which a first point and a second point of the triangle lie, a second reflecting surface lies on a straight line on which a third point and the first point of the triangle lie, and a third reflecting surface lies on a straight line on which the second point and the third point of the triangle lie, characterized in that:
the beam path of the triple reflection arrangement is crossed,
the second reflecting surface is used as the second of the three reflecting surfaces for reflection of a focused beam and the first reflecting surface is used as the first or third of the three reflecting surfaces for reflection,
the first reflecting surface and the second reflecting surface are disposed at an acute angle relative to each other,
the first reflecting surface and the third reflecting surface are disposed at an obtuse angle CBD relative to each other,
there is a normal from the second point of the triangle to the second reflecting surface, and
for the triple reflection arrangement there is an angle gamma between a marginal ray of an incoming or outgoing beam and the second reflecting surface, and the angle gamma is less than 12° (degrees).

* * * * *